(12) United States Patent
Baltes et al.

(10) Patent No.: US 9,468,906 B2
(45) Date of Patent: Oct. 18, 2016

(54) POROUS INORGANIC BODY

(71) Applicant: BASF SE, Ludwigshafen (DE)

(72) Inventors: Christian Baltes, Lampertheim (DE);
Tobias Rosendahl, Mannheim (DE);
Igor Shishkov, Mannheim (DE);
Torsten Mäurer, Lambsheim (DE);
Wolfgang Rohde, Speyer (DE); Martin Kraus, Westfield, NJ (US); Norbert Güntherberg, Speyer (DE); Isa Alexandra Queiroz Da Fonseca, Ludwigshafen (DE); Alfons Jochum, Ludwigshafen (DE); Siegbert Bouche, Rülzheim (DE)

(73) Assignee: BASF SE, Ludwigshafen (DE)

( * ) Notice: Subject to any disclaimer, the term of this patent is extended or adjusted under 35 U.S.C. 154(b) by 409 days.

(21) Appl. No.: 13/780,310

(22) Filed: Feb. 28, 2013

(65) Prior Publication Data

US 2013/0231493 A1  Sep. 5, 2013

Related U.S. Application Data

(60) Provisional application No. 61/605,805, filed on Mar. 2, 2012.

(51) Int. Cl.
*C07D 303/00* (2006.01)
*B01J 21/00* (2006.01)
(Continued)

(52) U.S. Cl.
CPC ............. *B01J 21/04* (2013.01); *B01J 21/16* (2013.01); *B01J 23/688* (2013.01); *B01J 35/023* (2013.01);
(Continued)

(58) Field of Classification Search
CPC .......... B01J 23/02; B01J 23/04; B01J 23/78; B01J 21/04; B01J 21/08; B01J 21/10; B01J 21/12; B01J 21/14; C07D 303/04

USPC ....... 502/100, 327, 328, 330, 332, 336, 341, 502/355, 415, 439; 549/513
See application file for complete search history.

(56) References Cited

U.S. PATENT DOCUMENTS 5,063,195 A   11/1991   Jin et al.
5,976,454 A   11/1999   Sterzel et al.
(Continued)

FOREIGN PATENT DOCUMENTS

CN   1034678 C   4/1997
CN   1216316 C   8/2005
(Continued)

OTHER PUBLICATIONS

International Search Report for PCT/IB2013/051598, dated Nov. 7, 2013.
(Continued)

*Primary Examiner* — Cam N. Nguyen
(74) *Attorney, Agent, or Firm* — Drinker Biddle & Reath LLP

(57) ABSTRACT

The present invention relates to a porous inorganic body comprising pores A having a pore size $S_A$ in the range of from 0.005 to 20 micrometer and a total pore volume $V_A$, and comprising pores B having a pore size $S_B$ in the range of from more than 20 to 1000 micrometer and a total pore volume $V_B$, wherein the total pore volume of the pores having a pore size in the range of from 0.005 to 1000 micrometer is $V_C$ and wherein the ratio $R_A = V_A/V_C$ is in the range of from 0.3 to 0.7 as determined via mercury intrusion porosimetry.

31 Claims, 9 Drawing Sheets

(51) Int. Cl.

| | | |
|---|---|---|
| *B01J 21/04* | (2006.01) | |
| *B01J 25/00* | (2006.01) | |
| *B01J 29/00* | (2006.01) | |
| *B01J 23/00* | (2006.01) | |
| *B01J 23/02* | (2006.01) | |
| *B01J 23/06* | (2006.01) | |
| *B01J 23/08* | (2006.01) | |
| *B01J 23/40* | (2006.01) | |
| *B01J 23/42* | (2006.01) | |
| *B01J 23/56* | (2006.01) | |
| *B01J 23/58* | (2006.01) | |
| *B01J 23/70* | (2006.01) | |
| *B01J 23/74* | (2006.01) | |
| *B01J 20/00* | (2006.01) | |
| *C07D 301/00* | (2006.01) | |
| *C07D 301/10* | (2006.01) | |
| *B01J 21/16* | (2006.01) | |
| *B01J 23/68* | (2006.01) | |
| *B01J 35/02* | (2006.01) | |
| *B01J 35/04* | (2006.01) | |
| *B01J 37/02* | (2006.01) | |
| *C04B 38/00* | (2006.01) | |
| *B01J 37/08* | (2006.01) | |
| *C04B 111/00* | (2006.01) | |

(52) U.S. Cl.
CPC ............ *B01J 35/04* (2013.01); *B01J 37/0201* (2013.01); *C04B 38/00* (2013.01); *C07D 301/00* (2013.01); *C07D 301/10* (2013.01); *B01J 37/08* (2013.01); *C04B 2111/0081* (2013.01); *C04B 2111/00129* (2013.01); *Y02P 20/52* (2015.11); *Y10T 428/131* (2015.01)

(56) References Cited

U.S. PATENT DOCUMENTS

| | | | |
|---|---|---|---|
| 8,314,049 B2* | 11/2012 | Bubb et al. .................. 502/439 |
| 8,546,294 B2* | 10/2013 | Liu et al. ...................... 502/241 |
| 8,685,883 B2* | 4/2014 | Bryden et al. ................ 502/355 |
| 8,716,504 B2* | 5/2014 | Liu et al. ...................... 549/534 |
| 2003/0128178 A1 | 7/2003 | Murade |
| 2004/0059056 A1 | 3/2004 | Montanari et al. |
| 2004/0138059 A1 | 7/2004 | Euzen et al. |
| 2004/0138483 A1* | 7/2004 | Rubinstein .................. 549/536 |
| 2008/0255390 A1* | 10/2008 | Bosch et al. ................. 564/469 |
| 2009/0156394 A1* | 6/2009 | Horiuchi et al. ............. 502/216 |
| 2009/0198076 A1 | 8/2009 | Guckel |
| 2010/0056816 A1* | 3/2010 | Wallin et al. ................. 549/534 |
| 2010/0267969 A1* | 10/2010 | Liu et al. ...................... 549/230 |
| 2010/0298133 A1* | 11/2010 | Takahashi et al. ........... 502/341 |

FOREIGN PATENT DOCUMENTS

| | | |
|---|---|---|
| CN | 1258567 C | 6/2006 |
| CN | 102365128 A | 2/2012 |
| EP | 0799810 A2 | 10/1997 |
| EP | 1283066 A1 | 2/2003 |
| EP | 1415712 A1 | 5/2004 |
| EP | 1927398 A1 | 6/2008 |
| EP | 2228115 A1 | 9/2010 |
| WO | WO-03/072244 A1 | 9/2003 |
| WO | WO-2006133187 A2 | 12/2006 |
| WO | WO-2011/109215 A1 | 9/2011 |

OTHER PUBLICATIONS

International Written Opinion for PCT/IB2013/051598, dated Nov. 7, 2013.

\* cited by examiner

POROUS INORGANIC BODY

CROSS-REFERENCE TO RELATED APPLICATIONS

This application claims benefit (under 35 USC 119(e)) of U.S. Provisional Application 61/605,805, filed Mar. 2, 2012, which is incorporated by reference.

BACKGROUND OF THE INVENTION

The present invention relates to a porous inorganic body which at least has first pores A having a pore size $S_A$ in the range of from 0.005 to 20 micrometer, and second pores B having a pore size $S_B$ in the range of from more than 20 to 1000 micrometer. The first pores A have a total pore volume $V_A$, and the second pores B have a total pore volume $V_B$. According to the present invention, the total pore volumes of all pores A and B, i.e. the pores having a pore size in the range of from 0.005 to 1000 micrometer, is $V_C$. The inorganic body of the present invention is characterized in that the ratio $V_A/V_C$ which is referred to as $R_A$ is in the range of from 0.3 to 0.7. Further, the present invention relates to a process for the preparation of a porous inorganic body, preferably the porous inorganic body described above, which process is characterized in that it is carried out in a temperature-controllable extruder wherein the starting materials are added in specific zones of the extruder. Yet further, the present invention relates to the use of the inorganic porous body, in particular as catalyst or catalyst support. Still further, the present invention relates to a temperature-controllable extruder as such.

BACKGROUND PRIOR ART

Porous inorganic bodies granulates are attractive catalyst carriers because of high accessibility of reactive sites compared to conventional, non-porous extruded bodies. It is often desired to provide a highly porous inorganic body, in particular in case the inorganic body is used as catalyst or catalyst carrier. In these cases, it is desired that the inorganic body possesses large transport pores. Such large pores facilitate the transport of the reagents, especially in the course of diffusion-limited catalyzed reactions, and decrease the pressure drop. Yet further, it is often additionally desired to provide a highly porous inorganic catalyst carrier possessing not only large transport pores as mentioned above, but also smaller pores. In these instances, the inorganic body would have an at least bimodal pore size distribution over a broad pore size range.

WO 2006/133187 describes a catalyst carrier which comprises non-platelet alumina and/or a bond material, which has a surface area of at least 1 m²/g, a total pore volume and a pore size distribution such that at least 80 percent of the total pore volume is contained in pores with diameters in the range of from 0.1 to 10 micrometers, and at least 80 percent of the pore volume contained in the pores with diameters in the range of from 0.1 to 10 micrometer is contained in pores with diameters in the range of from 0.3 to 10 micrometers. This carrier is obtained via a process comprising forming a mixture comprising a) from 50 to 95 weight percent of a first particulate alpha-alumina having a median particle size (d50) of from 5 to 100 micrometer; b) from 5 to 50 weight percent of a second particulate alpha-alumina having a d50 which is less than the d50 of the first particulate alpha-alumina and which is in the range of from 1 to 10 micrometer; and c) an alkaline earth metal silicate bond material; the weight percent values being based on the total weight of the alpha-alumina in the mixture; and firing the mixture to form the carrier. The ethylene oxide catalyst prepared on basis of the carrier showed good selectivity. The drawback of the method of carrier preparation is necessarily pre-mixing of the multi-component reaction mixture prior to extrusion. Moreover, the carrier obtained had >80% of pore volume contained in the pores with diameters in the range of from 0.1 to 10 micrometers, what could be problematic in terms of material transport, where considerably larger pores, e.g. >50 or even >100 micrometer, may be necessary.

WO 03/072244 A1 discloses that the selectivity and activity of a silver-based olefin epoxidation catalyst is found to be a function of the pore size distribution in the alumina carrier on which it is deposited. Specifically it is found advantageous to provide a carrier which has a minimum of very large pores, (greater than 10 micrometers) and a water absorption of 35 to 55 percent and a surface area of at least 1.0 m²/g. Specifically, it describes a carrier for a catalyst for the epoxidation of an olefin characterized by: the carrier comprising at least 95 percent alpha-alumina with a surface area of from 1.0 to 2.6 m²/g and a water absorption of from 35 to 55 percent, having pores which are distributed such that at least 70 percent of the pore volume is in the form of pores having pore diameters from 0.2 to 10 micrometers and pores with diameters between 0.2 and 10 micrometer provide a volume of at least 0.27 mL/g of the carrier. The claimed method of making such a carrier is characterized by: forming a mixture comprising: a) from 50 to 90 percent by weight of a first particulate alpha-alumina having an average particle size (d50) of from 10 to 90 micrometer; b) from 10 to 50 percent by weight, based on the total alpha alumina weight, of a second particulate alpha alumina having an average particle size (d50) of from 2 to 6 micrometers; c) from 2 to 5 percent by weight of an alumina hydrate; d) from 0.2 to 0.8 percent of an amorphous silica compound, measured as silica; and e) from 0.05 to 0.3 percent of an alkali metal compound measured as the alkali metal oxide; all percentages being based on the total alpha-alumina content of the mixture, and then forming the mixture into particles and firing the particles at a temperature of from 1250 to 1470° C. to form the carrier. Although the active catalyst prepared from the carrier of the invention operated at lower temperatures and afforded 81.9-82.5% selectivity, it does not provide reaction data about a catalyst prepared from a catalyst carrier possessing additional pores with a size of more than 100 micrometer. In addition, the multistep mixing of the starting materials followed by shaping the particles into a definite form in a separate step is expensive and time consuming.

EP-A-1 927 398 describes a catalyst for the production of ethylene oxide, comprising: a carrier containing alpha-alumina as the main component which has at least two peaks in the range of pore diameter of 0.01-100 micrometers and at least one peak of the above peaks is present in the range of pore diameter of 0.01-1.0 micrometer in the pore distribution measured by mercury porosimetry; and a catalyst component is supported on the carrier. Selectivities up to 82.6% to ethylene oxide can be obtained using a catalyst operation at 10% conversion and 232° C. prepared from a catalyst carrier according to this application. However, no carrier was reported here with a considerable pore volume assigned to pores with a size of more than 100 micrometer.

Therefore, it is an object of the present invention to provide novel inorganic bodies having such at least bimodal pore size distribution with a considerable pore volume assigned to pores with a size of more than 100 micrometer.

EP-A-0 799 810 describes a continuous process for producing open-celled, inorganic sintered foam products which process comprises:
a) converting slip material comprising sinterable inorganic powder, a fluid, vaporizable material which makes this slip material capable of flow and, if desired, a material forming blowing gas into a foamed product in a foaming step with liberation of the blowing gas;
b) subjecting this foamed product to a treatment which essentially makes the slip material incapable of flow and forms an open-pored intermediate body, with steps a. and b. being able to proceed essentially simultaneously;
c) removing material remaining from the fluid material and any further material from the intermediate body to form a green foam body; and
d) sintering the green foam body to form the open-celled, inorganic sintered foam product.

According to EP-A-0 799 810, for preparing the ceramic mass, a liquid phase is first introduced into the extruder as shown in FIG. 2. Then, the inorganic powder is added by a loss-in-weight system and is mixed with the liquid phase. Such a dosage procedure could lead to problems if the process is scaled-up since it could cause to the easier return flow of the slurry if a sudden pressure increase due to tail backing occurs. Although the process in EP-A-0 799 810 provides a method to continuously obtain foamed extrudates, it must be further optimized to run smoothly. Moreover, EP-A-0 799 810 does not describe simultaneous addition of several solid components which might be beneficial for better process stability and reproducibility.

Therefore, it is a further object of the present invention to provide a simple and effective continuous process to make porous inorganic bodies.

It is yet a further object of the present invention to provide an extruder being especially suitable for carrying out this process and/or preparing this inorganic body.

SUMMARY OF THE INVENTION

Thus, the present invention relates to a porous inorganic body comprising pores A having a pore size $S_A$ in the range of from 0.005 to 20 micrometer and a total pore volume $V_A$, and comprising pores B having a pore size $S_B$ in the range of from more than 20 to 1000 micrometer and a total pore volume $V_B$, wherein the total pore volume of the pores having a pore size in the range of from 0.005 to 1000 micrometer is $V_C$ and wherein the ratio $R_A = V_A/V_C$ is in the range of from 0.3 to 0.7 as determined via mercury intrusion porosimetry according to DIN 66133.

Also, the present invention relates to a process for the preparation of a porous inorganic body, preferably of a porous inorganic body comprising pores A having a pore size $S_A$ in the range of from 0.005 to 20 micrometer and a total pore volume $V_A$, and comprising pores B having a pore size $S_B$ in the range of from more than 20 to 1000 micrometer and a total pore volume $V_B$, wherein the total pore volume of the pores having a pore size in the range of from 0.005 to 1000 micrometer is $V_C$ and wherein the ratio $R_A = V_A/V_C$ is in the range of from 0.3 to 0.7 as determined via mercury intrusion porosimetry according to DIN 66133, said process comprising
a) supplying a sinterable inorganic powder, preferably an alumina powder, more preferably an alpha alumina powder, at a first zone of a temperature-controllable zoned extruder comprising a die head and at least 3 zones;
b) supplying an aqueous solution comprising a binder or an aqueous suspension comprising a binder at a second zone of the zoned extruder downstream of the first zone;
c) mixing the sinterable inorganic powder and the aqueous solution or suspension in the extruder to yield a mixture;
d) heating the mixture in the zoned extruder up to a temperature of at most 200° C. at an essentially constant volume, thereby increasing the pressure and at least partially vaporizing the water comprised in the mixture to yield a pressurized mixture;
e) expanding the pressurized mixture into a volume which is at a pressure lower than that of the pressurized mixture to yield a non-flowable intermediate body after extrusion via the die head;
f) optionally subjecting the intermediate body to a temperature of from 100° C. to 120° C. thereby removing remaining water from the intermediate body to yield a green body;
g) calcining the green body or the intermediate body at a temperature of from 300° C. to 1100° C.;
h) optionally sintering the calcined green body at a temperature higher than the calcination temperature up to at most 2000° C. to yield the porous inorganic body;
wherein said process is preferably a continuous process.

Also, the present invention relates to an inorganic body as obtainable or obtained by this process.

Also, the present invention relates to the use of an inorganic body as described above as a catalyst carrier, preferably as a carrier of a catalyst for the preparation of ethylene oxide, more preferably as a carrier of a silver based catalyst for the preparation of ethylene oxide.

DETAILED DESCRIPTION OF THE INVENTION

Inorganic Body

Figure 1:
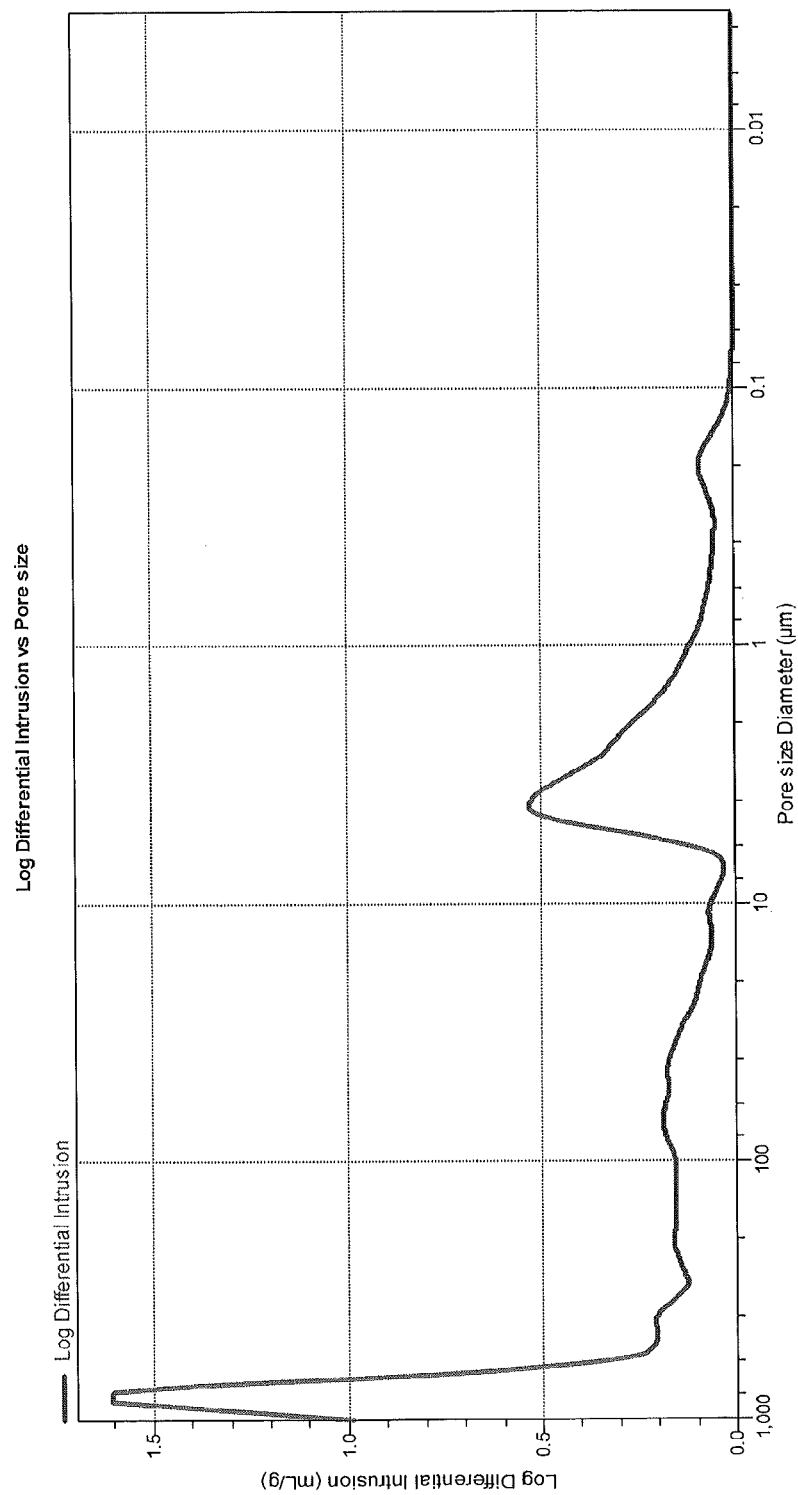
FIG. 1-FIG. 5 are diagrams depicting the differential intrusion of the sintered sample, i.e. the inorganic body according to Examples 1-5.

As mentioned above, the present invention relates to a porous inorganic body comprising pores A having a pore size $S_A$ in the range of from 0.005 to 20 micrometer and a total pore volume $V_A$, and comprising pores B having a pore size $S_B$ in the range of from more than 20 to 1000 micrometer and a total pore volume $V_B$, wherein the total pore volume of the pores having a pore size in the range of from 0.005 to 1000 micrometer is $V_C$ and wherein the ratio $R_A = V_A V_C$ is in the range of from 0.3 to 0.7 as determined via mercury intrusion porosimetry according to DIN 66133.

According to a preferred embodiment of the present invention, $R_A$ is in the range of from 0.31 to 0.69, more preferably in the range of from 0.32 to 0.68, more preferably in the range of from 0.33 to 0.67, more preferably in the range of from 0.34 to 0.66, more preferably in the range of from 0.35 to 0.65.

These values of $R_A$ are generally fulfilled for all pores with $S_A$ in the range of from 0.005 to 20 micrometer. Preferably, for these values of $R_A$ to be fulfilled, $S_A$ is preferably in the range of from 0.01 to 20 micrometer, more preferably in the range of from 0.02 to 20 micrometer, more preferably in the range of from 0.05 to 20 micrometer, more preferably in the range of from 0.1 to 20 micrometer.

Further preferably, for these values of $R_A$ to be fulfilled, $S_A$ is in the range of from 0.2 to 20 micrometer, more preferably in the range of from 0.3 to 20 micrometer, more preferably in the range of from 0.4 to 20 micrometer.

Therefore, according to a preferred embodiment, the present invention relates to above-defined inorganic body, wherein $S_A$ is in the range of from 0.4 to 20 micrometer and $R_A$ is in the range of from 0.35 to 0.65.

According to these preferred embodiments according to which $S_A$ is in the range of from 0.4 to 20 micrometer and $R_A$ is in the range of from 0.35 to 0.65, the ratio of the volume $V_A'$ of the pores of the inorganic body having a pore size of from 0.005 to less than 0.4 micrometer, relative to $V_C$, is preferably in the range of from 0 to 0.05, preferably in the range of from 0 to 0.04. This ratio is referred to herein as $R_A'$. Therefore, according to a preferred embodiment, the present invention relates to above-defined inorganic body wherein $S_A$ is in the range of from 0.4 to 20 micrometer and $R_A$ is in the range of from 0.35 to 0.65 and wherein $R_A'$ is in the range of from 0 to 0.05.

Further, generally, the pores B have any pore size $S_B$ which is in the range of from more than 20 to 1000 micrometer. Preferably, $S_B$ is in the range of from 25 to 1000 micrometer, more preferably in the range of from 40 to 1000 micrometer, more preferably in the range of from 60 to 1000 micrometer, more preferably in the range of from 80 to 1000 micrometer, more preferably in the range of from 100 to 1000 micrometer.

Therefore, according to a preferred embodiment, the present invention relates to above-defined inorganic body, wherein $R_A$ is in the range of from 0.3 to 0.7, preferably in the range of from 0.35 to 0.65, with $S_A$ being in the range of from 0.005 to 20 micrometer, more preferably in the range of from 0.1 to 20 micrometer, more preferably in the range of from 0.4 to 20 micrometer, and $S_B$ is in the range of from 100 to 1000 micrometer.

Further according to the present invention, the inorganic body has an at least bimodal pore size distribution. The term "at least bimodal pore size distribution" as used in this context of the present invention relates to the measurement of the differential intrusion as a function of the pore size, as determined via mercury intrusion porosimetry according to DIN 66133. An at least bimodal pore size distribution exists if according to this determination method, the differential intrusion contains at least one peak in the pore size range of from 0.005 to 20 micrometer and further contains at least one peak in the pore size range of from 20 to 1000 micrometer.

Therefore, the present invention also relates to the inorganic body as defined above, wherein the differential intrusion determined via mercury intrusion porosimetry according to DIN 66133 as a function of the pore size contains at least one peak in the pore size range of from 0.005 to 20 micrometer and at least one peak in the pore size range of from 20 to 1000 micrometer.

According to a preferred embodiment of the present invention, said differential intrusion contains at least one peak, preferably one peak or two peaks in the pore size range of from 0.01 to 20 micrometer, preferably in the pore size range of from 0.05 to 20 micrometer, more preferably in the pore size range of from 0.1 to 20 micrometer, more preferably in the pore size range of from 0.2 to 20 micrometer. Even more preferably, at least one peak is in the pore size range of from 1 to 20 micrometer.

Generally, there no specific restrictions concerning the specific surface area (BET) of the inorganic body of the present invention. Preferably, the specific surface area (BET) as determined according to DIN ISO 9277 is at least 0.1 m$^2$/g, preferably at least 0.2 m$^2$/g, more preferably at least 0.5 m$^2$/g. More preferably, the specific surface area (BET) as determined according to DIN ISO 9277 is in the range of from 0.1 to 2.5 m$^2$/g, more preferably in the range of from 0.3 to 2.0 m$^2$/g, more preferably in the range of from 0.5 to 1.5 m$^2$/g, more preferably in the range of from 0.7 to 1.3 m$^2$/g, more preferably in the range of from 0.8 to 1.2 m$^2$/g.

Further, the inorganic body according to the present invention exhibits a water absorption in the range of from 0.1 to 2 ml/g. Preferred water absorptions are in the range of from 0.2 to 1.5 ml/g, with the range of from 0.4 to 1.0 ml/g being especially preferred. The determination of the water absorption is described in detail in Reference Example 1.

Concerning the composition of the inorganic body of the present invention, no specific restrictions exist provided that above-defined characteristics are fulfilled. Preferably, the inorganic body of the present invention comprises at least one of alumina, silica, zirconia, titania, and mixed oxides thereof. More preferably, at least 75 weight-%, more preferably at least 80 weight-%, more preferably at least 85 weight-%, more preferably at least 90 weight-%, more preferably at least 95 weight-%, more preferably at least 99 weight-% of the inorganic body consist of at least one of alumina, silica, zirconia, titania, and mixed oxides thereof, preferably of at least one of alumina and silica, more preferably alumina. Conceivable modifications of alumina are, for example, alpha alumina, gamma alumina, delta alumina, eta alumina, theta alumina, kappa alumina and mixtures of two or more thereof. Especially preferred is alpha alumina.

Therefore, according to a preferred embodiment, the present invention relates to above-defined inorganic body, wherein at least 95 weight-% thereof, preferably at least 99 weight-% thereof are comprised of alumina, preferably alpha alumina.

In addition, preferably in addition to alumina, more preferably in addition to alpha alumina, the inorganic body of the present invention may comprise at least one further element, for example at least one alkali metal—such as Li and/or Na and/or K and/or Rb and/or Cs—and/or at least one alkaline earth metal—such as Mg and/or Ca and/or Sr and/or Ba—and/or at least one transition metal—such as Ti and/or Mn and/or Fe and/or Co and/or Zn and/or Mo—, and/or at least an element of the 13th and/or 14th and/or 15th and/or 16th group of the periodic table—such as B and/or Ga and/or Si and/or Ge and/or Sn and/or S. More preferably, the inorganic body of the present invention comprises at least one element selected from the group consisting of alkali metals, alkaline earth metals, silicon, and iron. Among the alkali metals, Na is especially preferred. Therefore, according to an even more preferred embodiment, the present invention relates to above-defined inorganic body, comprising at least one element selected from the group consisting of sodium, silicon, and iron.

As far as the amounts of these elements, additionally contained in the inorganic body of the present invention, are concerned, no specific restrictions exist provided that the amount of preferably alumina, more preferably alpha alumina contained in the inorganic body is within above-defined ranges. Preferably the inorganic body of the present invention comprises of from 200 to 750 weight-ppm of sodium, up to 600 weight-ppm, preferably of from 350 to 550 weight-ppm of silicon, and up to 100 weight-ppm of iron, based on the total weight of the inorganic body, calculated as element and as determined via elemental analysis.

According to especially preferred embodiments of the present invention, the inorganic body of the present invention is used as catalyst or as catalyst carrier. Therefore, the geometry of the inorganic body of the present invention is not subject to specific restrictions and can exhibit any form suitable for a desired application. According to preferred embodiments of the present invention, the inorganic body has the geometry of a strand such as a hollow strand, a star, a ball, a ring, or a cylinder. More preferably, the inorganic body of the present invention has the geometry of a cylinder. Even more preferably, the preferred cylinders have a length in the range of from 3 to 20 mm, preferably of from 4 to 15 mm, more preferably of from 5 to 10 mm, an outer diameter in the range of from 2 to 20 mm, preferably of from 3 to 15 mm, more preferably of from 5 to 10 mm, and a ratio of outer diameter (in mm) relative to wall thickness (in mm) in the range of from 1 to 15, preferably of from 2 to 10, more preferably of from 2.5 to 4.5.

According to especially preferred embodiments, the cylinders have the following geometries (outer diameter× length×inner diameter, in each case in millimeter): 5×5×2, 6×6×3, 7×7×3, 8×8×3, 8×8.5×3, 8×8.5×3.5, 8.5×8×3.5, 8.5× 8×3, 9×9×3, 9.5×9×3, 9.5×9×3.5. Every of these specifications is to be understood as comprising a tolerance in the range of from plus/minus 0.5 mm.

As mentioned above, the inorganic body of the present invention is preferably used as catalyst or catalyst carrier. Especially preferable is the use as catalyst carrier. While there are no specific restrictions concerning the reactions for which the inorganic body is used as catalyst or as catalyst carrier, the use as catalyst carrier of a catalyst for the preparation of ethylene oxide is especially preferred. Even more preferably, the inorganic body is used as catalyst carrier of a silver based catalyst for the preparation of ethylene oxide.

Therefore, the present invention also relates to the inorganic body as defined above for use as a catalyst carrier or as a catalyst, preferably as a catalyst carrier of a silver based catalyst for the preparation of ethylene oxide. Further, the present invention relates to the use of the inorganic body as defined above as a catalyst carrier, preferably as a carrier of a catalyst for the preparation of ethylene oxide, more preferably as a carrier of a silver based catalyst for the preparation of ethylene oxide.

Preferred Use as Catalyst Carrier

In case the inorganic body of the present invention is used as catalyst carrier for a silver based catalyst which is preferably used for the production of ethylene oxide via epoxidation of ethylene, the silver and optionally further promoters which may include, among others, Re, W, Li, Cs or S, the silver and the at least one promoter can be applied onto the inorganic body of the present invention by all conceivable methods, including, for example, impregnation and spraying methods, with impregnation methods being preferred. Preferably, catalysts are prepared containing, based on the final catalyst, silver in an amount of from 1 to 50 weight-%, preferably from 5 to 35 weight-%, more preferably from 10 to 25 weight-%, calculated as elemental silver.

Preferably, the catalyst is prepared via impregnation with a preferably aqueous solution containing silver and at least one promoter, more preferably silver and at least one promoter selected from the group consisting of Re, W, Li, Cs and S, more preferably silver and the promoters Re, W, Li, Cs and S.

Preferred catalysts prepared based on the inorganic body of the present invention contain Re in an amount of from 50 to 1200 weight-ppm, preferably from 100 to 1000 weight-ppm, more preferably from 150 to 600 weight-ppm, more preferably from 200 to 500 weight-ppm, based on the total catalyst weight and calculated as element.

Preferred catalysts prepared based on the inorganic body of the present invention contain W in an amount of from 10 to 800 weight-ppm, preferably from 20 to 500 weight-ppm, more preferably from 50 to 300 weight-ppm, more preferably from 80 to 250 weight-ppm, based on the total catalyst weight and calculated as element.

Preferred catalysts prepared based on the inorganic body of the present invention contain Li in an amount of from 50 to 700 weight-ppm, preferably from 75 to 400 weight-ppm, more preferably from 100 to 250 weight-ppm, based on the total catalyst weight and calculated as element.

Preferred catalysts prepared based on the inorganic body of the present invention contain Cs in an amount of from 50 to 1500 weight-ppm, preferably from 100 to 800 weight-ppm, more preferably from 200 to 700 weight-ppm, more preferably from 250 to 600 weight-ppm, based on the total catalyst weight and calculated as element.

Preferred catalysts prepared based on the inorganic body of the present invention contain S in an amount of from 1 to 100 weight-ppm, preferably from 1 to 50 weight-ppm, more preferably from 2 to 30 weight-ppm, more preferably from 5 to 20 weight-ppm, based on the total catalyst weight and calculated as element.

Therefore, the present invention also relates to the inorganic body as defined above for use as a catalyst carrier of a silver based catalyst, preferably of a silver based catalyst for the production of ethylene oxide, wherein the catalyst comprises of from 1 to 50 weight-% of silver, from 50 to 1200 weight-ppm of Re, from 10 to 800 weight-ppm of W, from 50 to 700 weight-ppm of Li, from 50 to 1500 weight-ppm of Cs, and from 1 to 100 weight-ppm of S, in each case based on the total weight of the catalyst and calculated as element.

Further, the present invention relates to the inorganic body as defined above, comprised as a catalyst carrier in a silver based catalyst, preferably in a silver based catalyst for the production of ethylene oxide, wherein the catalyst comprises of from 1 to 50 weight-% of silver, from 50 to 1200 weight-ppm of Re, from 10 to 800 weight-ppm of W, from 50 to 700 weight-ppm of Li, from 50 to 1500 weight-ppm of Cs, and from 1 to 100 weight-ppm of S, in each case based on the total weight of the catalyst and calculated as element.

The term "total weight of the catalyst" as used in this context of the present invention relates to the total weight of the calcined catalyst to be employed in the ethylene oxide production reaction.

Still further, the present invention relates to a process for the production of ethylene oxide wherein as epoxidation catalyst, a silver based catalyst is employed comprising, as catalyst carrier, the inorganic body as defined above and further comprising of from 1 to 50 weight-% of silver, said catalyst preferably further comprising from 50 to 1200 weight-ppm of Re, from 10 to 800 weight-ppm of W, from 50 to 700 weight-ppm of Li, from 50 to 1500 weight-ppm of Cs, and from 1 to 100 weight-ppm of S, in each case based on the total weight of the catalyst and calculated as element.

Process

The present invention also relates to a process for the preparation of a porous inorganic body wherein the porous inorganic body is preferably a porous inorganic body as defined above.

According to this process, a sinterable inorganic powder is supplied at a first zone of an extruder. This sinterable inorganic powder forms the basis of the porous inorganic body finally obtained. At a second zone of the extruder, a binder is supplied which is preferably used to prevent a collapse of the finally obtained, preferably foamed extrudates when water is at least partially evaporated from them. According to the present, it was found that if the second zone of the extruder at which the binder is added, is located downstream of the first zone at which the sinterable inorganic powder is supplied, the process allows for avoiding accumulation of inorganic powder, for avoiding the build-up of crusts due to said accumulation, for example at the inlet, and thus for running the extrusion process which is preferably a continuous process homogeneously and without interruptions and/or pulsations. The term "downstream" as used in this context of the present invention relates to an extruder design wherein said second zone is closer to the extruder plate (also referred to herein as die plate) than the first zone. Generally, the second zone can be controlled with respect to the temperature within said second zone independently of said first zone which in turn is also temperature-controllable. Said second zone of the extruder can be positioned immediately after said first zone. It is also conceivable that said second zone and said first zone are separated from each other be at least one additional extruder zone wherein at least one of this/these additional zone/s can be temperature-controllable and/or design as a zone at which at least one component of the extrudable mass can be supplied.

Therefore, the present invention relates to a process for the preparation of a porous inorganic body, preferably of a porous inorganic body as defined above, said process comprising a) supplying a sinterable inorganic powder, preferably an alumina powder, more preferably an alpha alumina powder, at a first zone of a temperature-controllable zoned extruder comprising a die head and at least 3 zones;
b) supplying an aqueous solution comprising a binder or an aqueous suspension comprising a binder at a second zone of the zoned extruder downstream of the first zone;
c) mixing the sinterable inorganic powder and the aqueous solution or suspension in the extruder to yield a mixture;
d) heating the mixture in the zoned extruder up to a temperature of at most 200° C. at an essentially constant volume, thereby increasing the pressure and at least partially vaporizing the water comprised in the mixture to yield a pressurized mixture;
e) expanding the pressurized mixture into a volume which is at a pressure lower than that of the pressurized mixture to yield a non-flowable intermediate body after extrusion via the die head;
f) optionally subjecting the intermediate body to a temperature of from 100° C. to 120° C. thereby removing remaining water from the intermediate body to yield a green body;
g) calcining the green body or the intermediate body at a temperature of from 300° C. to 1100° C.;
h) optionally sintering the calcined green body at a temperature higher than the calcination temperature up to at most 2000° C. to yield the porous inorganic body;

wherein said process is preferably a continuous process.

Step a)

According to step a) of the process according to the present invention, a sinterable inorganic powder is supplied at a first zone of the extruder. The term "first zone" as used in this context of the present invention does not exclude extruder designs wherein there is at least one additional zone upstream of said first zone, wherein at least one of this/these additional zone/s upstream of said first zone can be temperature-controllable and/or designed as a zone at which at least one component of the extrudable mass can be supplied. Thus, according to the present invention, it is not excluded that at least one component is supplied at a zone upstream of said first zone with the proviso that the component or the components supplied as binder are supplied at a second zone downstream of said first zone. According to a preferred embodiment of the present invention, no component of the extrudable mass prepared in the extruder is supplied at a zone upstream of said first zone. Further, the term "first zone" as used in this context of the present invention does not exclude extruder designs wherein said first zone consists of two or more separate zones of the temperature-controllable extruder wherein each zone may be temperature-controllable. Preferably, said first zone is one temperature-controllable zone of the extruder.

Therefore, the present invention also relates to the process as defined above, wherein no component of the extrudable mass prepared in the temperature-controllable zoned extruder is supplied at a zone upstream of the first zone.

According to the present invention, no specific limitations exist concerning the chemical nature of the inorganic powder provided that the inorganic powder is sinterable and allows for the preparation of a porous inorganic body. Among others, metal powders, mineral powders, ceramic powders, metal carbide powders, metal nitride powders, and mixtures of two or more of these powders can be supplied. The term "powder" as used in this context of the present invention refers to chemical compounds typically having particles with a d50 value in the range of from 0.01 to 500 micrometer, preferably of from 0.5 to 100 micrometer.

Suitable metal powders include, for example, iron, cobalt, nickel, copper, silver, titanium, steel powders or alloy powders of iron-, nickel- or cobalt-based alloys. Preferably, ceramic powders are supplied. Suitable ceramic powders include, for example, alumina, silica, titania, zirconia, optionally partially or completely stabilized with magnesium oxide or yttrium oxide, mixed oxides of Al and/or Si and/or Ti and/or Zr optionally partially or completely stabilized with magnesium oxide or yttrium oxide silicon carbide, silicon nitride, including usual sintering auxiliaries such as alumina and yttrium oxide, cordierite, mullite, kaolin, calcinated kaolin, acid-activated bleaching earth, clays and montmorrilonit-containing clays, dioctahedral smectites and, included those obtained via an acid activations, tungsten carbide, titanium carbide, tantalum carbide, vanadium carbide, titanium nitride, and tantalum nitride. More preferably, alumina and/or silica are supplied as sinterable inorganic powder. More preferably, alumina is supplied as sinterable inorganic powder. Concerning alumina, generally no restrictions exist which phase is supplied. Conceivable modifications of alumina are, for example, alpha alumina, gamma alumina, delta alumina, eta alumina, theta alumina, kappa alumina and mixtures of two or more thereof. Especially preferred is alpha alumina.

Therefore, the present invention relates to a process as defined above, wherein in step a), alumina and/or silica, preferably alumina, more preferably alpha alumina is supplied as sinterable inorganic powder. Even more preferably, the alpha alumina supplied at the first zone has a d50 value in the range of from 0.01 to 500 micrometer, more preferably of from 0.5 to 100 micrometer, and/or, preferably and, a specific surface area (BET) as determined according to DIN ISO 9277 in the range of from 0.1 to 500 m²/g.

According to the present invention, it is also possible that only a portion of the sinterable inorganic powder is supplied at the first zone of the extruder with the proviso that the binder is supplied at a second zone downstream of said first zone. In this case, it is preferred that at least 50 weight-%, preferably more than 50 weight-%, more preferably at least 75 weight % of the overall amount of sinterable inorganic powder are supplied at the first zone. While it is conceivable that the portion of the inorganic sinterable powder which is not supplied at the first zone is supplied at the second zone, it is preferred that this remaining portion is supplied at at least one zone downstream of said second zone with the proviso that the remaining portion is added at at least zone upstream of the zone where step d) is carried out.

The temperature at which the sinterable inorganic powder is supplied at the first zone is preferably in the range of from 20 to 50° C., more preferably in the range of from 25 to 45° C., more preferably in the range of from 30 to 40° C.

The amount of sinterable inorganic powder supplied is not specifically restricted. Preferably, the sinterable inorganic powder is supplied in an amount so that the mixture heated in step d) comprises from 50 to 90 weight-% of the inorganic powder, relative to the total weight of the mixture.

Step b)

According to step b) of the process according to the present invention, an aqueous solution comprising a binder or an aqueous suspension comprising a binder is supplied at a second zone of the zoned extruder downstream of the first zone. The term "second zone" as used in this context of the present invention does not exclude extruder designs wherein said second zone consists of two or more separate zones of the temperature-controllable extruder wherein each zone may be temperature-controllable, with the proviso that these zones are downstream of the first zone. Preferably, said second zone is one temperature-controllable zone of the extruder downstream of the first zone which is preferably one temperature-controllable zone of the extruder.

Suitable binders include, for example, water-soluble polymers such as polyvinyl alcohol, starch, methylated starch, alginates, hydroxymethylcellulose, hydroxyethylcellulose, polyacrylic acid, polyacrylamide, polyethyleneimine, polyvinylamine, polyvinylformamide or polyvinylpyrrolidone. Another class of binders comprises aqueous polymer dispersions based on styrene/butadiene copolymers or acrylates. It may also be conceivable to use aluminum hydroxide as inorganic binder. Further, it is possible to supply a mixture of two or more binders at the second zone of the extruder according to step b). Preferably, water soluble polymers are supplied as binder, with polyacrylic acid, polyacrylamide, polyethyleneimine, polyvinylamine, polyvinylformamide and polyvinylpyrrolidone being more preferred. More preferably, the binder supplied comprises or consists of polyvinylpyrrolidone.

Therefore, the present invention relates to the process as defined above, wherein in step b), the binder is selected from the group consisting of polyacrylic acid, polyacrylamide, polyethyleneimine, polyvinylamine, polyvinylformamide, polyvinylpyrrolidone, and a mixture of two or more thereof.

The temperature at which the aqueous solution comprising the binder or the aqueous suspension comprising the binder is supplied at the second zone is generally essentially the same as, preferably higher than the temperature of the first zone. Preferably, the temperature at which the aqueous solution comprising the binder or the aqueous suspension comprising the binder is supplied at the second zone is in the range of from 40 to 90° C., more preferably in the range of from 50 to 80° C., more preferably from 55 to 65° C.

While there are no specific restrictions concerning the amount of binder supplied at the second zone, it is preferred to supply the aqueous solution comprising the binder or the aqueous suspension comprising the binder in an amount so that the mixture in the extruder heated in step d) comprises of from 2 to 20% weight-%, preferably from 5 to 15 weight-%, of the binder relative to the amount of sinterable inorganic powder comprised in said mixture.

Step c)

According to step c) of the process according to the present invention, the sinterable inorganic powder and the aqueous solution or suspension are mixed in the extruder to yield a mixture. The mixing according to step c) is generally accomplished by suitable mixing means with which the extruder, in particular the extruder screw is equipped. Preferably, said mixing is carried out in the at least one zone of the extruder at which the binder is supplied, and/or in at least one extruder zone downstream of said zone/s.

The temperature at which the mixing is carried out is generally essentially the same as or higher than the temperature of the second zone. Preferably, the temperature at which the mixing is carried out is in the range of from 40 to 90° C., more preferably in the range of from 60 to 90° C.

Plasticizing Agent

According to the process of the present invention, at least one plasticizing agent can be supplied at at least one zone of the extruder. Most preferably, the at least one plasticizing agent supplied at an extruder zone upstream of the zone where the mixture is heated to a temperature of at most 200° C. according to step d). More preferably, the at least one plasticizing agent is supplied at an extruder zone upstream of the zone where the mixture is prepared according to step c).

Therefore, the present invention relates to above-defined process wherein prior to step d), preferably prior to step c), at least one plasticizing agent is added.

Suitable plasticizing agents include, for example, graphites or composition containing graphites, polyoxyethylene-polyoxypropylene-block-copolymers, cellulose ethers or esters especially those soluble in water and having a viscosity range of preferably between 500 and 100000 mPa*s and/or a number average molecular weight between 10000 and 220000 g/mol, and combinations of two or more thereof. Especially preferred plasticizing agents are graphites and cellulose ethers. Generally, it may be possible that a plasticizing agent acts as pore forming agent. This is believed to apply, for example, to graphites and cellulose ethers, polyoxyethylene-polyoxypropylene-block-copolymers.

Therefore, the present invention relates to the process as defined above, wherein prior to step d), preferably prior to step c), at least one plasticizing agent is added, which plasticizing agent is selected from the group consisting of graphites, cellulose ethers, and a mixture thereof, said plasticizing agent more preferably being a cellulose ether.

While there are no specific restrictions concerning the amount of plasticizing agent supplied, it is preferred to supply the plasticizing agent in an amount so that the mixture in the extruder heated in step d) comprises of from 0.5 to 40 weight-%, preferably from 2 to 40 weight-%, more preferably from 10 to 40 weight-%, more preferably from 20 to 40 weight-% of the at least one plasticizing agent, relative to the sinterable inorganic powder. In case graphite is supplied as plasticizing agent, it is preferred to supply the plasticizing agent in an amount of from 20 to 40 weight-%, more preferably from 25 to 35 weight-%, relative to the sinterable inorganic powder.

While there are no specific restriction concerning the zone or the zones where the at least one plasticizing agent is supplied, it is preferred to supply it at a zone different from the zone at which the aqueous solution comprising the binder or the aqueous suspension comprising the binder is supplied. In particular in case graphite is supplied as plasticizing agent, it is preferred to supply it at at least one zone downstream of the zone at which the aqueous solution comprising the binder or the aqueous suspension comprising the binder is supplied.

Therefore, the present invention relates to the process as defined above, wherein prior to step d), preferably prior to step c), at least one plasticizing agent is added, said plasticizing agent being supplied at as zone downstream of said second zone, which plasticizing agent is preferably selected from the group consisting of graphites, cellulose ethers, and a mixture thereof, said plasticizing agent more preferably being a cellulose ether.

The temperature at which the plasticizing agent is supplied generally depends on the zone or the zones at which it is supplied. In case the plasticizing agent is added at a zone downstream of said second zone, the temperature is preferably higher than the temperature of said second zone. Preferably, the temperature at which the plasticizing agent is supplied at a zone downstream of said second zone is in the range of from 70 to 95° C., more preferably in the range of from 80 to 95° C., more preferably from 85 to 95° C.

Pore Forming Agent

According to the process of the present invention, at least one pore forming agent can be supplied at at least one zone of the extruder. Most preferably, the at least one pore forming agent is supplied at an extruder zone upstream of the zone where the mixture is heated to a temperature of at most 200° C. according to step d).

Therefore, the present invention relates to above-defined process wherein prior to step d), at least one pore forming agent and/or at least one pore forming agent precursor is added. The term "pore forming agent precursor" as used in this context of the present invention relates to a chemical compound from which, once contained in the mixture in the extruder, a pore forming agent is obtained, for example by chemical reaction.

Suitable pore forming agents include, for example, organic particles or granulates capable of being removed via calcination. Preferred pore forming agents are graphites, polyoxyethylene-polyoxypropylene-block-copolymers, cellulose ethers, cellulose esters, polymers and copolymers of styrene, polymers or copolymers of acrylic and/or methacrylic acid and its esters, and combinations of two or more thereof. Especially preferred pore forming agents are graphites and cellulose ethers. Generally, it may be possible that a pore forming agent acts as plasticizing agent. This is believed to apply, for example, to graphites and cellulose ethers, but also to polyoxyethylene-polyoxypropylene-block-copolymers.

Therefore, the present invention relates to the process as defined above, wherein prior to step d), at least one pore forming agent is added, which pore forming agent is selected from the group consisting of graphites, cellulose ethers, and a mixture thereof, said pore forming agent more preferably being a graphite.

While there are no specific restrictions concerning the amount of pore forming agent supplied, it is preferred to supply the pore forming in an amount so that the mixture in the extruder heated in step d) comprises of from 1 to 50 weight-%, preferably from 2 to 40 weight-%, more preferably from 3 to 40 weight-% of the at least one pore forming agent, relative to the sinterable inorganic powder. In case graphite is supplied as pre forming agent, it is preferred to supply the pore forming agent in an amount of from 1 to 40 weight-%, more preferably from 2 to 35 weight-%, relative to the sinterable inorganic powder.

While there are no specific restriction concerning the zone or the zones where the at least one pore forming agent is supplied, it is preferred to supply it at a zone different from the zone at which the aqueous solution comprising the binder or the aqueous suspension comprising the binder is supplied. In particular in case cellulose ether is supplied as pore forming agent, it is preferred to supply it at at least one zone upstream of the zone at which the aqueous solution comprising the binder or the aqueous suspension comprising the binder is supplied, more preferably at said first zone at which the sinterable inorganic powder is supplied.

Therefore, the present invention relates to the process as defined above, wherein prior to step d), at least one pore forming agent is added, said pore forming agent being supplied at as zone upstream of said second zone, which pore forming agent is preferably selected from the group consisting of graphites, cellulose ethers, and a mixture thereof, said pore forming agent more preferably being a graphite.

The temperature at which the pore forming plasticizing agent is supplied generally depends on the zone or the zones at which it is supplied. In case the pore forming agent is added at a zone upstream of said second zone, the temperature is preferably lower than the temperature of said second zone. Preferably, the temperature at which the pore forming agent is supplied at a zone upstream of said second zone is identical to the temperature at which the sinterable inorganic powder is supplied since both the inorganic powder and the pore forming agent are supplied at said first zone.

Surface Active Compound/Blowing Agent Precursor

According to the process of the present invention, at least one surface active compound and/or at least one blowing agent precursor can be supplied at at least one zone of the extruder. Preferably, the at least one surface active compound and/or the at least one blowing agent precursor is/are supplied at at least one zone upstream of the zone where the mixture is heated to a temperature of at most 200° C. according to step d). More preferably, the at least one surface active compound and/or the at least one blowing agent precursor is/are supplied at at least one zone upstream of the zone where the mixing is carried out according to step c). Even more preferably, the at least one surface active compound and/or the at least one blowing agent precursor is/are supplied at the zone where the aqueous solution comprising the binder or the aqueous suspension comprising the binder is supplied. Generally, it is possible to supply the at least one surface active compound and/or the at least one blowing agent precursor in separate streams or as one combined stream. Preferably, the at least one surface active compound and/or the at least one blowing agent precursor are supplied comprised in the aqueous solution comprising the binder or in the aqueous suspension comprising the binder.

Therefore, the present invention relates to above-defined process wherein prior to step d), preferably prior to step c), more preferably in step b), at least one surface active compound and/or at least one blowing agent precursor is added, preferably via the aqueous solution supplied in step b).

Suitable surface active compounds include, for example, anionic, cationic or none-ionic surfactants. Preferably, the surface active compounds are none-ionic. More preferably, the surface active compounds have HLB (hydrophilic-lipophilic balance) values in the range of from 7 to 19; the term "HLB value" as used in this context of the present invention is to be understood as defined as $HLB=20\times(1-M_l/M)$, with $M_l$ being the molecular mass of the lipophilic portion of a given surface active molecule, and M being the molecular mass of the complete molecule. More preferably, the surface active compounds are selected from the group consisting of polyoxyethylene-polyoxypropylene-block-copolymers, alkoxylated sugars, alcohols, alkoxylated alcohols such as ethoxylated alcohols, and mixtures of two or more thereof. More preferably, the surface active compounds are selected from the group consisting of ethoxylated fatty alcohols, oxo alcohols, Guerbet alcohols, i.e. highly branched aliphatic alcohols of the formula $H_3C(CH_2)_nCHR^1CH_2OH$ wherein $R^1$ is a linear alkyl radical having n-1 carbon atoms and wherein n is a number of from 5 to 11, and mixtures of two or more thereof. The degree of ethoxylation is preferably in the range of from 1 to 80. Therefore, the present invention relates to above-defined process wherein prior to step d), preferably prior to step c), more preferably in step b), at least one surface active compound and/or at least one blowing agent precursor is added, preferably via the aqueous solution supplied in step b), wherein the at least one surface active compound is selected from the group consisting of polyoxyethylene-polyoxypropylene-block-copolymers, alkoxylated sugars, alcohols, alkoxylated alcohols, and mixtures of two or more thereof, preferably selected from the group consisting of alkoxylated alcohols, more preferably selected from the group consisting of ethoxylated alcohols.

Suitable blowing agent precursors include, for example, water, ammonium carbonate, ammonium carbamate, ammonium hydrogencarbonate or mixtures of tow or more thereof such as mixtures of water and ammonium carbonate, mixtures of water and ammonium carbamate or mixtures of water and ammonium hydrogencarbonate. Most preferably, water or a mixture of water and ammonium carbonate is supplied as blowing agent precursor, with water being especially preferred.

According to the present invention, the blowing agent precursor can also be pre-mixed with the inorganic powder, and the resulting mixture can be added to the first zone. Also, it is possible to add the blowing agent precursor together with the inorganic powder without pre-mixing.

Therefore, the present invention relates to above-defined process wherein prior to step d), preferably prior to step c), more preferably in step b), at least one surface active compound and/or at least one blowing agent precursor is added, preferably via the aqueous solution supplied in step b), wherein the at least one blowing agent precursor is water or a mixture of water and ammonium carbonate, preferably water.

Hence, the present invention relates to above-defined process wherein prior to step d), preferably prior to step c), more preferably in step b), at least one surface active compound and/or at least one blowing agent precursor is added, preferably via the aqueous solution supplied in step b), wherein the at least one blowing agent precursor is water or a mixture of water and ammonium carbonate, preferably water, and wherein the at least one surface active compound is selected from the group consisting of polyoxyethylene-polyoxypropylene-block-copolymers, alkoxylated sugars, alcohols, alkoxylated alcohols, and mixtures of two or more thereof, preferably selected from the group consisting of alkoxylated alcohols, more preferably selected from the group consisting of ethoxylated alcohols.

While there are no specific restrictions concerning the amount of surface active compound supplied, it is preferred to supply the surface active compound in an amount so that the mixture in the extruder heated in step d) comprises of from 0.5 to 10 weight-%, preferably from 1 to 9 weight-%, more preferably from 2 to 8 weight-% of the at least one surface active compound, relative to the sinterable inorganic powder.

While there are no specific restrictions concerning the amount of blowing agent precursor supplied, it is preferred to supply the blowing agent precursor in an amount so that the mixture in the extruder heated in step d) comprises of from 20 to 90 weight-%, preferably from 30 to 85 weight-%, more preferably from 40 to 80 weight-% of the at least one blowing agent precursor, relative to the sinterable inorganic powder.

While there are no specific restriction concerning the zone or the zones where the at least one surface active compound and/or the at least one blowing agent precursor is supplied, it is especially preferred to supply it at the zone at which the aqueous solution comprising the binder or the aqueous suspension comprising the binder is supplied.

Since at the second zone, the aqueous solution comprising the binder or the aqueous suspension comprising the binder is supplied, the water comprised in said solution and/or said suspension is to be regarded as blowing agent precursor. Depending on the amount of said solution or said suspension supplied, it may be necessary, in order to achieve the preferred amounts of blowing agent precursor defined above, to add further water.

Step d)

According to step d), the mixture is heated in the zoned extruder up to a temperature of at most 200° C. at an essentially constant volume, thereby increasing the pressure and at least partially vaporizing the water comprised in the mixture to yield a pressurized mixture.

According to preferred embodiments of the present invention, said heating of the mixture according to step d) is carried out at from 2 to 6, more preferably from 3 to 5, more preferably from 3 or 4, more preferably in 3 extruder zones. Thereby, the temperature of the first extruder zone of step d) is at least 85° C., preferably in the range of from 85 to 110° C., more preferably in the range of from 90 to 105° C., more preferably in the range of from 95 to 105° C. Generally, the temperature at the first extruder zone of step d) is equal to or higher than, more preferably higher than, the temperature of the zones upstream the first zone of step d). The temperature of the last extruder zone of step d) which is preferably the extruder zone directly at the extruder plate (die plate) is generally equal to or higher than, preferably higher than, the temperature at the first extruder zone of step d), preferably in the range of from 105 to 150° C., more preferably of from 105 to 140° C., more preferably of from 105 to 130° C.

Temperature Profile

Upstream the extruder zones of step d), the steps a) to c) are carried out using preferably of from 2 to 5 extruder zones, more preferably of from 3 to 4 extruder zones. Therefore, the process according to the present invention is preferably carried out in a temperature-controllable extruder having of from 4 to 11, preferably of from 4 to 10, more preferably of from 6 to 8 such as 6, 7, or 9 extruder zones. Preferably, the temperature profile along said zones, starting from the first zone of step a) and ending with the last zone of step d), is within the range of from 20 to 150° C., more preferably from 25 to 140° C., more preferably from 30 to 130° C.

Step e)

According to step s) of the present invention, the pressurized mixture obtained from step d) is expanded into a volume which is at a pressure lower than that of the pressurized mixture to yield a non-flowable intermediate body. Further according to the present invention, the pressurized mixture which is obtained in the last zone of the extruder upstream the die head is expanded by passing the pressurized mixture through the die head directly to at least one nozzle with which the die plate is equipped, from which nozzle the intermediate body, i.e. the extruded body is obtained.

Surprisingly, it was found that minimizing the dead volume of the die plate leads to improved process results. Therefore, the present invention relates to above-defined process, wherein the dead volume of the die head of the temperature-controllable zoned extruder is less than 40 ml, preferably less than 35 ml, more preferably less than 30 ml. More preferably, the dead volume of the die head is at most 25 ml, more preferably at most 15 ml, more preferably in the range of from 5 to 15 ml.

Further preferred results were obtained using a nozzle with having, at the output side, sharp edges. In certain cases, the results could be even improved in case said sharp edges and/or, preferably and, the outer nozzle surface were polished prior to the extrusion process. Therefore, the present invention also relates to above-defined process, wherein the die head of the temperature-controllable zoned extruder is equipped with a nozzle having an output side and wherein the nozzle has a wall width at the output side of at most 1 mm, preferably 0.5 mm at most, and most preferably 0.25 mm at most.

In the following, preferred extruders according to the present invention are described.

Preferred Extruder

Further, the invention relates to a temperature-controllable extruder. The temperature-controllable extruder is suitable for carrying out the inventive process.

In an embodiment E1 of the temperature-controllable extruder, the extruder is a temperature-controllable zoned extruder comprising a die head, at least one extruder screw, a barrel in which the at least one extruder screw extends, and at least two zones including a first zone and a second zone provided downstream the first zone, wherein the extruder further comprises an inorganic powder inlet port and a binder inlet port located downstream the inorganic powder inlet port, wherein a dead volume between an end of the extruder screw is provided, the ratio of the dead volume and an inner radius of the barrel being at most 2000 mm², wherein the die head further comprises at least one nozzle feeding channel extending from the dead volume and at least one nozzle with an inner nozzle channel directly connected to the nozzle feeding channel, and wherein the inner nozzle channel of the at least one nozzle has an inner channel with an angled ending.

In an embodiment E2 of the inventive extruder as given in E1, the die head comprises an extruder plate having at least one recess into which the end of the extruder screw extends at least partly.

In an embodiment E3 of the inventive extruder as given in E1 or E2, at an output side of the nozzle, the nozzle is provided with a wall width of 1 mm±10% at most, preferably 0.5 mm±10% at most, and most preferably 0.25 mm±10% at most. In a particular embodiment, the wall width is 0.2 mm±10%.

In an embodiment E4 of the inventive extruder as given in E1, E2 or E3, a distance between the extruder screw and the nozzle is less than 20 mm±10%, preferably less than 15 mm±10% and more preferably less than 12 mm±10%, more preferably less than 10 mm±10%. In a particular embodiment, this distance is 6 mm±10%. This distance refers to the distance between screws and the thread of the nozzle.

In an embodiment E5 of the inventive extruder as given in E1, E2, E3 or E4, the inner nozzle channel directly connected to the nozzle feeding channel together have a total channel length of 60 mm at most, preferably 50 mm at most, more 40 mm at most. An especially preferred channel length is in the range of from 20 to 40 mm, more preferably from 30 to 40 mm.

In an embodiment E6 of the inventive extruder as given in any of embodiments E1 to E5, the at least one nozzle has a smoothened front surface at the output side and/or a smoothened circumferential outer surface at the output side.

In an embodiment E7 of the inventive extruder as given in any of embodiments E1 to E6, the die head further comprises a cooling channel, in particular in connection with an inner chamber within the die head.

In an embodiment E8 of the inventive extruder as given in any of embodiments E1 to E7, the extruder is a double screw extruder and comprises two extruder screws in parallel, both being located in the barrel.

Each of the embodiments E1 to E8 can form the basis of the embodiments depicted and described with reference to the figures.

With reference to the embodiments given herein and particular with reference to embodiment E1, the inventive extruder can be provided with at least one of the following features. The zones of the extruder, in particular the first and the second zones, each extend longitudinally along the extruder in a direction directed towards the die head. The zones of the extruder, in particular the first and the second zones, are individually temperature-controllable. Each of the zones is temperature controlled and is adapted to be maintained at a predefined temperature. The zones are adapted to be individually controlled to maintain distinct temperatures. Preferably, the temperature of along each zone is constant. The temperature control can be provided by heating and/or cooling. In particular, a heat transfer medium can be provided within a channel and/or a cavity within the zones. The channels and/or the cavity for a temperature transfer medium and/or electric heaters individual for each zone are provided enabling the temperature-controllable zones. The channels for a temperature transfer medium and/or the electric heaters are in direct contact to the barrel or are provided within the barrel. At least one of the zones or all zones can be equipped with an electrical heating element for temperature control. Advantageously, the die head is provided with a temperature control as given above in the context of the temperature controlled zones. In particular, the die head can be provided with a channel and/or a cavity for a heat transfer medium, in particular a fluid or a liquid coolant like water. Advantageously, in each zone of the extruder, the barrel is adapted to be controlled at a set point temperature for this zone, wherein the temperature is substantially constant for each zone of the barrel.

The inorganic powder inlet port is preferably provided in the first zone. The binder inlet port is preferably provided in the second zone. An optional plasticizing agent inlet port can be provided upstream, downstream or at the same position as the inorganic powder inlet port in a longitudinal direction of the extruder directed towards the die head. The plasticizing agent inlet port can be provided at the same zone as the inorganic powder inlet port or in another zone of the extruder located upstream the binder inlet port or located between the first zone comprising the inorganic powder inlet port and the second zone comprising the binder inlet port.

The inner nozzle channel of each nozzle is defined by the interior surface of the nozzle. The nozzle further comprises an output side to which the inner nozzle channel extends. At the angled ending of the inner nozzle channel, the output side abuts to the interior surface forming a circumferential sharp edge. The sharp edge corresponds to radius of curvature of substantially zero, wherein the radius is provided in a plane comprising the longitudinal axis of the inner channel. The inner nozzle channel and the interior surface are preferably in cylindrical shape. The sharp edge follows a closed line, preferably a circle.

Preferably, the inorganic powder inlet port and in particular the optional plasticizing agent inlet port are adapted for receiving flowable solid powder substances. The powder inlet port of the first zone is adapted to receive inorganic powder, in particular the inorganic powder as used for the inventive process and/or as described herein. The inorganic powder inlet port is able to be used for transferring the inorganic powder into the barrel of the extruder. The inorganic powder inlet port is separated from the binder inlet port of the second zone along the longitudinal axis of the extruder. The optional plasticizing agent inlet port is adapted to receive a plasticizing agent as given herein, for example cellulose ether. In particular, the optional plasticizing agent inlet port is adapted to receive dissolved or dispensed in a liquid, in particular in form of an aqueous solution. Alternatively, the optional plasticizing agent inlet port is adapted to receive a flowing agent, in particular a rheology modification agent, in flowable solid form, in particular in form of a powder, for example cellulose ethers.

The binder inlet port is adapted to receive binder, in particular the binder as used for the inventive process and/or as described herein. Particularly, the binder is in liquid form, for example in form of an aqueous solution. Thus, the binder inlet port is adapted to receive a liquid and in particular an aqueous solution of the binder. The binder inlet port is able to be used for transferring a liquid comprising the binder into the barrel of the extruder. The binder inlet port is separated from inorganic powder inlet port and in particular from the optional plasticizing agent inlet port. In particular, the binder inlet port is separated from the zones in which the inorganic powder inlet port and, in case, the optional plasticizing agent inlet port are located, by a distance along the longitudinal axis of the extruder. The binder inlet port is able to be used for transfer of the binder agent into the barrel of the extruder.

With reference to the embodiments given herein and particular with reference to embodiment E2, the inventive extruder can be provided with at least one of the following features.

The dead volume of the inventive extruder is located within the recess. Further, the nozzle feeding channel extends from the recess, in particular from an apex of the recess, towards the nozzle. The feeding channel and/or the inner nozzle channel extend(s) along a longitudinal axis of the extruder screw. The nozzle feeding channel is provided by a nozzle slot extending through the recess, in particular at the apex of the recess. The nozzle is attached within the nozzle slot, preferably by a threaded connection. The recess is preferably in a convex shape, preferably in the shape of a cone and in particular in the shape of a rounded cone. The end of the extruder screw extending into the recess has an envelope substantially corresponding to the extent of the recess. Advantageously, the dead volume is provided between an apex area of the extruder screw and a corresponding apex area of the recess.

The ratio of the dead volume and the inner radius of the barrel is at most 2000 mm$^2$, preferably 1600 mm$^2$ at most, more preferably 1200 mm$^2$ at most, more preferably 1000 mm$^2$ at most. In particular embodiments, the ratio of the dead volume relative to the inner radius of the barrel is in the range of from 400 mm$^2$ to 1200 mm$^2$, more preferably from 400 mm$^2$ to 1200 mm$^2$. In an exemplifying embodiment, this ratio relates to an inner radius of the barrel of 10 to 25 mm and, in particular, to an inner radius of the barrel of 12.5 mm±10%. Further, by way of example, the dead volume is preferably 25000 mm$^3$ (equivalent to 25 ml) at most, more preferably 15000 mm$^3$ (equivalent to 15 ml) at most, more preferably from 5000 to 15000 mm$^3$ (equivalent to 5 to 15 ml). In another example, the dead volume is preferably 12500 mm$^3$ (equivalent to 12.5 ml) at most. As an example, the dead volume is 12000 mm$^3$±10%, equivalent to 12 ml±10%.

According to an alternative example, an extruder is used with a dead volume in that range of from 110 to 150 cm$^3$ of at most 150 cm$^3$ and 110 cm$^3$ at least, wherein the inner radius of the barrel is 20 mm±10%. In particular, the ratio can be 10000 mm$^2$ at least or 7000 mm$^2$ at least or 6000 mm$^2$ at least. In a specific example, the ratio is about 5500 mm$^2$ at most.

With such a small or negligible dead volume, in particular in comparison to the cross-sectional area of the nozzle, the mixture is provided with a high homogeneity. In particular, a small or negligible dead volume between extruder screw and the nozzle, in which the mixing effect of the extruder screw is reduced or negligible, avoids segregation effects of the mixture before entry into the nozzle.

With reference to the embodiments given herein and particular with reference to embodiment E3, the inventive extruder can be provided with at least one of the following features.

The wall width at the output side of the nozzle corresponds to a wall width of the nozzle at a front face of the nozzle at which the mixture is decompressed. It has been found that with reduced wall widths, the risk of nozzle blocking is significantly reduced. At the output side of the nozzle, an outlet opening is provided, in particular in the front face of the nozzle.

With reference to the embodiments given herein and particular with reference to embodiment E4, the inventive extruder can be provided with at least one of the following features.

The distance between the extruder screw and the nozzle is the distance between an apex of a front face of the extruder screw, and a point of the nozzle, which is closest to this apex of the extruder screw. This distance is small and preferably less than 20 mm. The small distance between the extruder screw and the nozzle leads to a significantly reduced dead volume and reduces segregation effects of the mixture before entry into the nozzle.

With reference to the embodiments given herein and particular with reference to embodiment E5, the inventive extruder can be provided with at least one of the following features.

The inner nozzle channel directly connected to the nozzle feeding channel together extend from the dead volume and, in particular, from the recess, to the output side of the nozzle. The output side of the nozzle is located at the end of the nozzle opposed to the nozzle feeding channel. The end of the nozzle opposed to the nozzle feeding channel extends into an ambiance being at standard pressure. Further, the output side of the nozzle directly adjoins to this ambiance. The mixture provided by the extruder extends at the output side of the nozzle when exiting the end of the nozzle opposed to the nozzle feeding channel.

With reference to the embodiments given herein and particular with reference to embodiment E6, the inventive extruder can be provided with at least one of the following features.

The smoothened front surface and/or the smoothened outer surface are polished surfaces or are surfaces with a anti-stick coating. The circumferential outer surface of the nozzle is tapered in a direction along the longitudinal axis of the nozzle and away from the die head. In particular, the nozzle is in the shape of a hollow truncated cone the truncation plane of which forming the front surface. The nozzle and in particular the inner nozzle channel has a longitudinal axis identical to the longitudinal axis (ie. the rotational axis) of the extruder screw.

With reference to the embodiments given herein and particular with reference to embodiment E7, the inventive extruder can be provided with at least one of the following features.

The inner chamber surrounds a section of the die head from which the nozzle extends. In particular, the inner chamber surrounds the nozzle feeding channel and/or a section of the inner nozzle channel within the cooling head. The inner chamber is in fluidic connection to the cooling channel. In particular, the cooling channel comprises a feeding channel and a discharge channel between which the inner chamber is located. The cooling channel is filled with a heat transfer medium, in particular a coolant or is adapted to be filled with a heat transfer medium, in particular a coolant. A pump can be provided for active cycling the temperature control medium. Further, a heat sink can be provided in order to remove the heat transferred by the heat transfer medium from the extruder.

With reference to the embodiments given herein and particular with reference to embodiment E8, the inventive extruder can be provided with at least one of the following features.

The two extruder screws of the inventive extruder are of the same size and are at the same position as regards the longitudinal axis of the extruder. For each of the screws, a dead volume is provided as given herein. Preferably, for each of the screws a recess as given herein is provided within the die head, wherein the ends of the extruder screws extend at least partly into the recess. For each dead volume, a nozzle as given herein is provided at the die head. Each of the volumes of the recesses is provided as given herein. Further, for each of the extruder screws, a nozzle feeding channel as given herein is provided in the die head.

In an alternative embodiment, for all extruder screws in the extruder, one dead volume at the die head is provided. In this embodiment, the dead volume is located at the center of the die head. One or more nozzle feeding channels connected to the dead volume are provided in the die head. For each nozzle feeding channels, a nozzle as given above is provided.

Further, the die head can comprise two or more nozzles for each extruder screw (one, two or more) within the extruder. For each nozzle, a nozzle feeding channel is provided within the die head. The two or more nozzles can be located vis-à-vis the end of the pertaining extruder screw.

In particular, the die head can comprise a plurality of nozzles. At least two, a subgroup or all of the nozzles can be in fluidic connection with the same dead volume. One or more dead volumes can be provided, wherein at least one of the dead volumes or all dead volumes are in fluidic connection with more than one nozzle or with a subgroup of nozzles as given above. A subgroup as well as a plurality of nozzles refers to at least two nozzles. The fluidic connection can be provided by a feeding channel as given above.

BRIEF DESCRIPTION OF THE FIGURES

FIG. 1-FIG. 5 are diagrams depicting the differential intrusion of the sintered sample, i.e. the inorganic body according to Examples 1-5.

Figure 6:
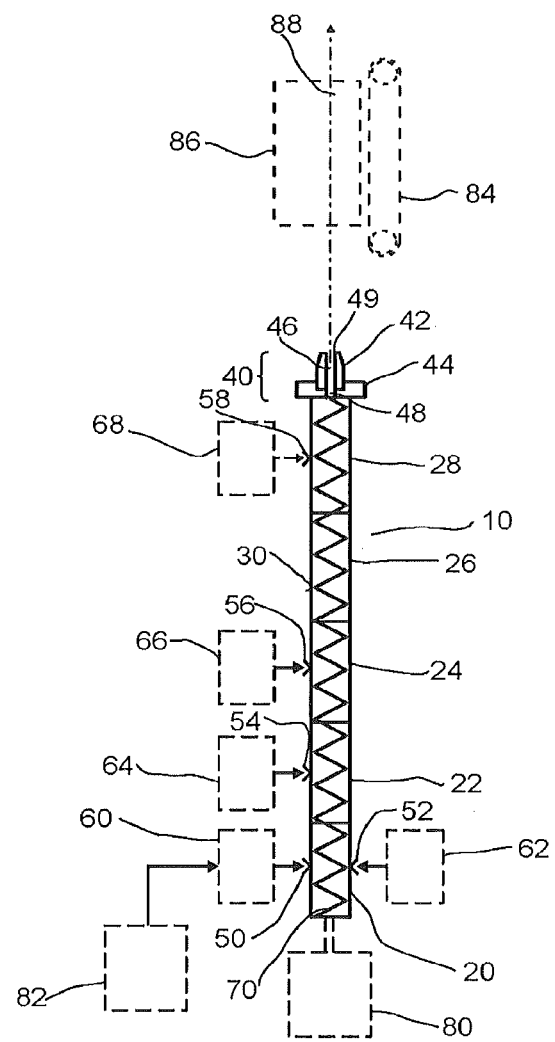
FIG. 6 symbolically depicts an embodiment of the extruder according to the invention and auxiliary components.

FIG. 6 symbolically depicts an embodiment of the extruder according to the invention and auxiliary components.

Figure 7:
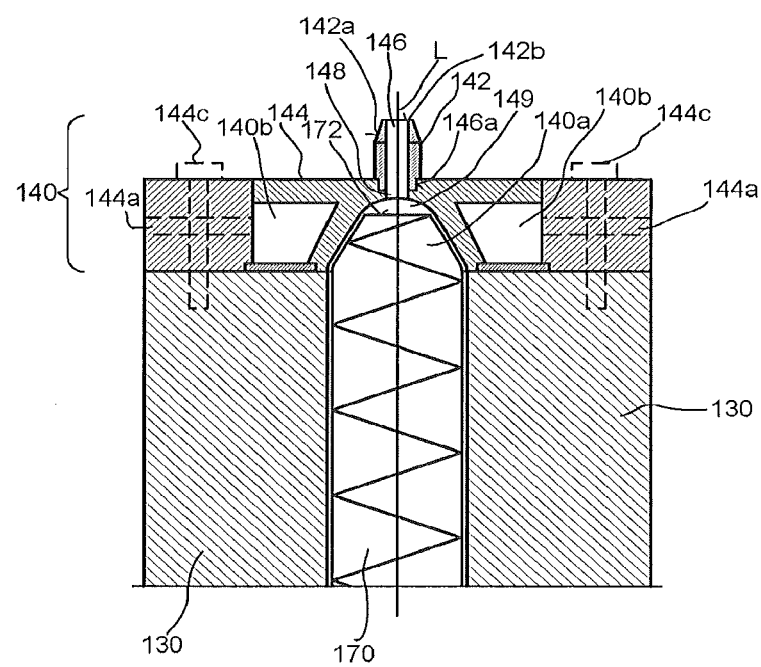
FIG. 7 depicts a die head of an embodiment of the extruder according to the present invention.

FIG. 7 depicts a die head of an embodiment of the extruder according to the present invention.

Figure 8:
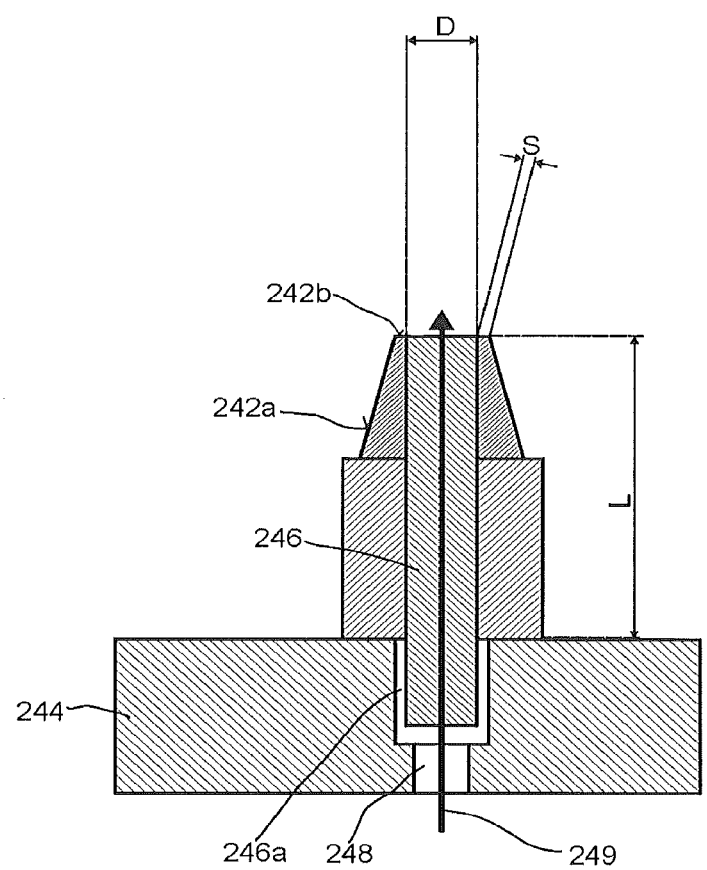
FIG. 8 shows a first embodiment of a nozzle of the inventive extruder.

FIG. 8 shows a first embodiment of a nozzle of the inventive extruder.

Figure 9:
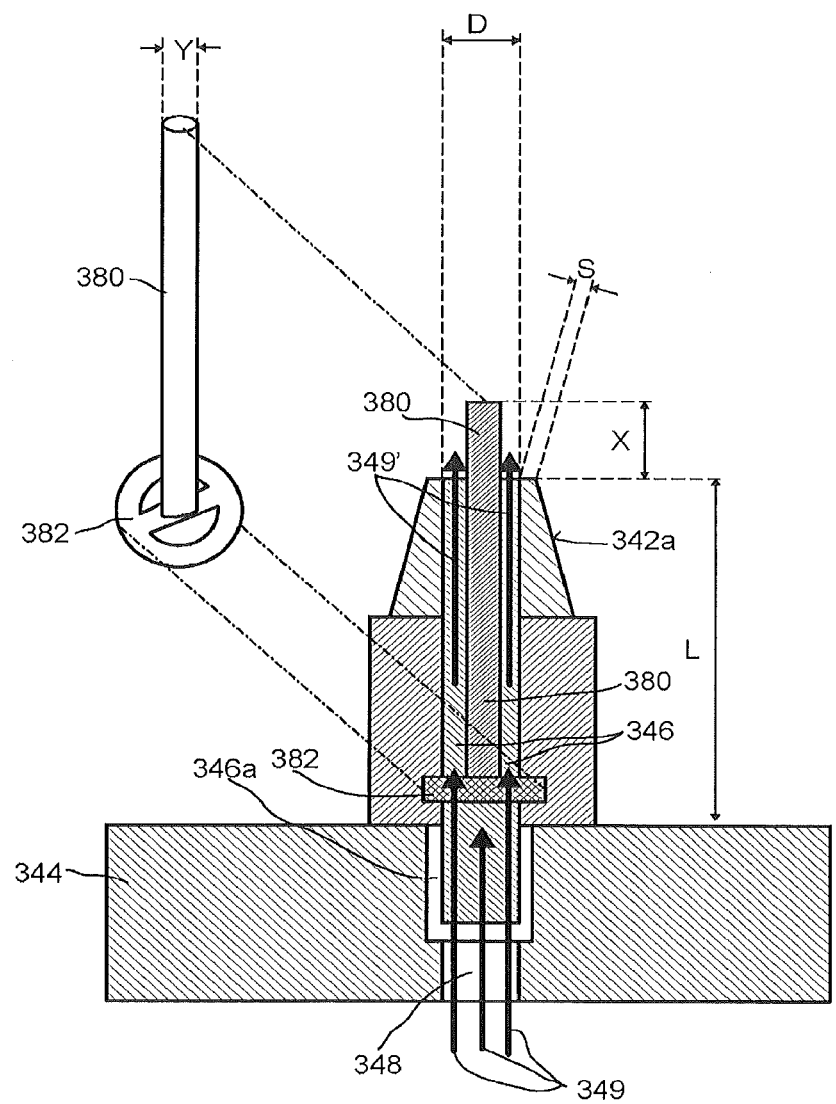
FIG. 9 shows a second embodiment of a nozzle of the inventive extruder.

FIG. 9 shows a second embodiment of a nozzle of the inventive extruder.

DETAILED DESCRIPTION OF THE DRAWINGS

FIG. 1 shows the differential intrusion of the sintered sample, i.e. the inorganic body according to Example 1 as a function of the pore size, as determined via mercury intrusion porosimetry according to DIN 66133. On the x axis, the pore size is shown in micrometer. On the y-axis, the differential intrusion is shown (logarithmic scale).

Figure 2:
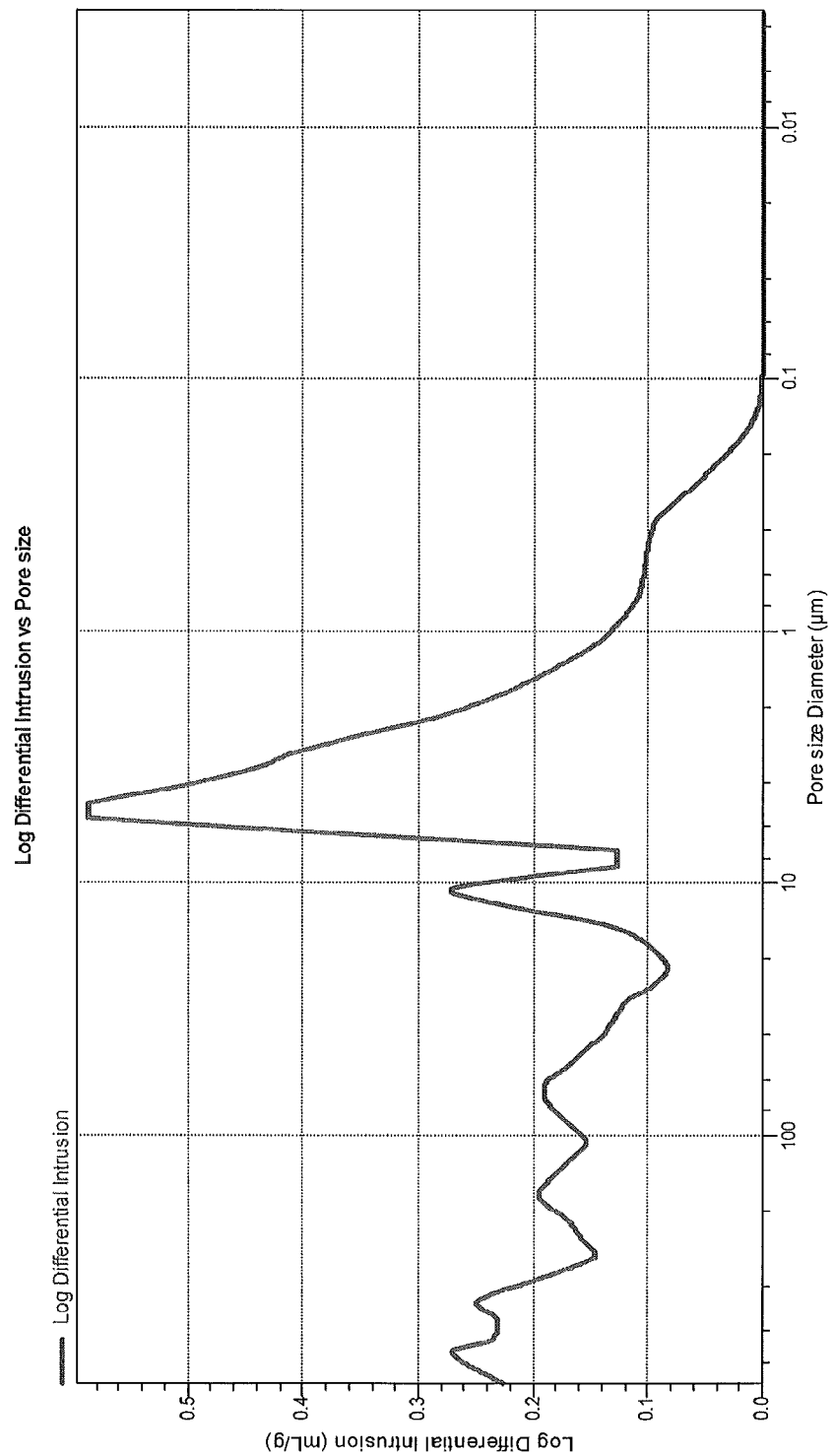

FIG. 2 shows the differential intrusion of the sintered sample, i.e. the inorganic body according to Example 2 as a function of the pore size, as determined via mercury intrusion porosimetry according to DIN 66133. On the x axis, the pore size is shown in micrometer. On the y-axis, the differential intrusion is shown (logarithmic scale).

Figure 3:
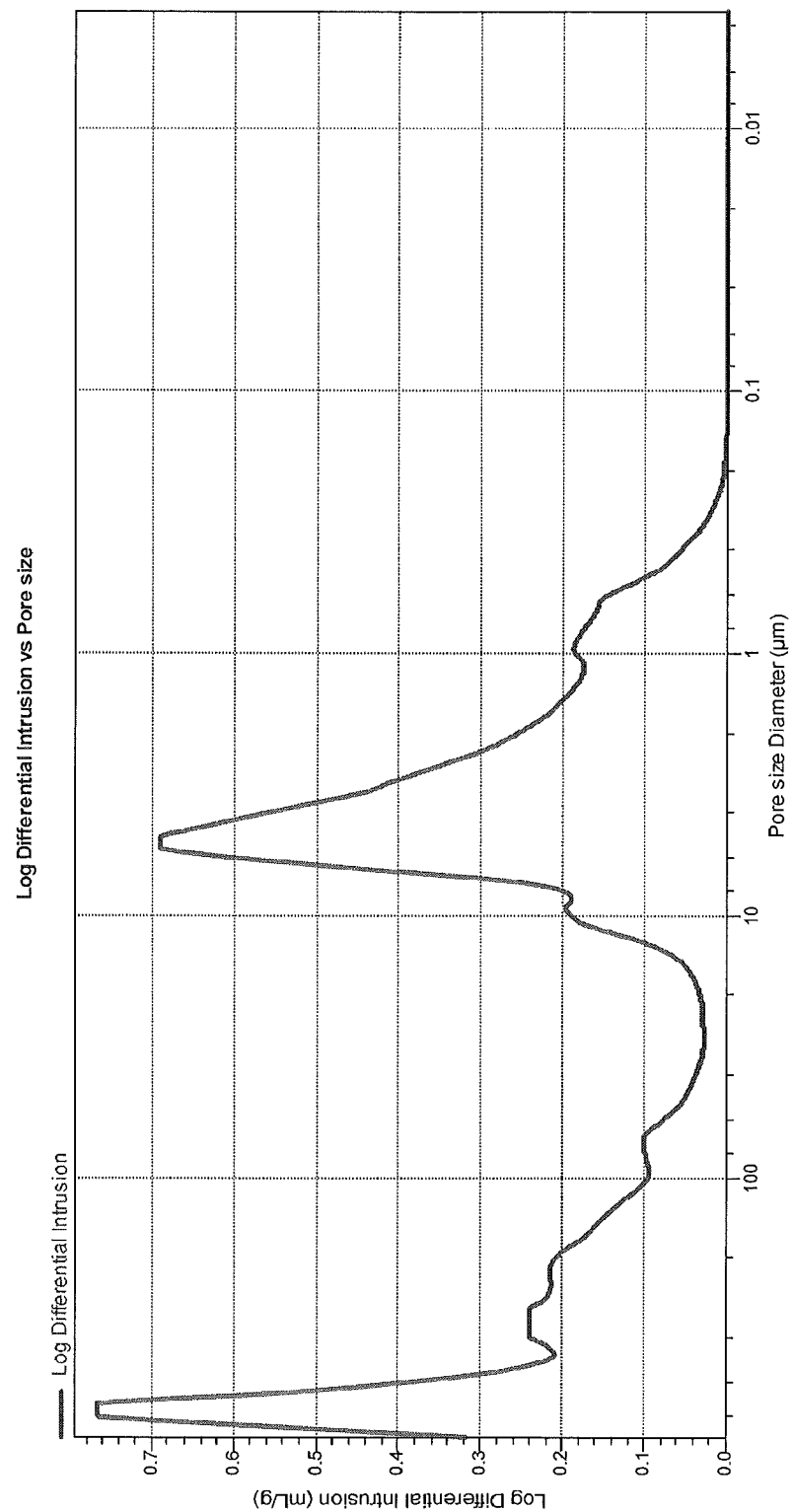

FIG. 3 shows the differential intrusion of the sintered sample, i.e. the inorganic body according to Example 3 as a function of the pore size, as determined via mercury intrusion porosimetry according to DIN 66133, On the x axis, the pore size is shown in micrometer. On the y-axis, the differential intrusion is shown (logarithmic scale).

Figure 4:
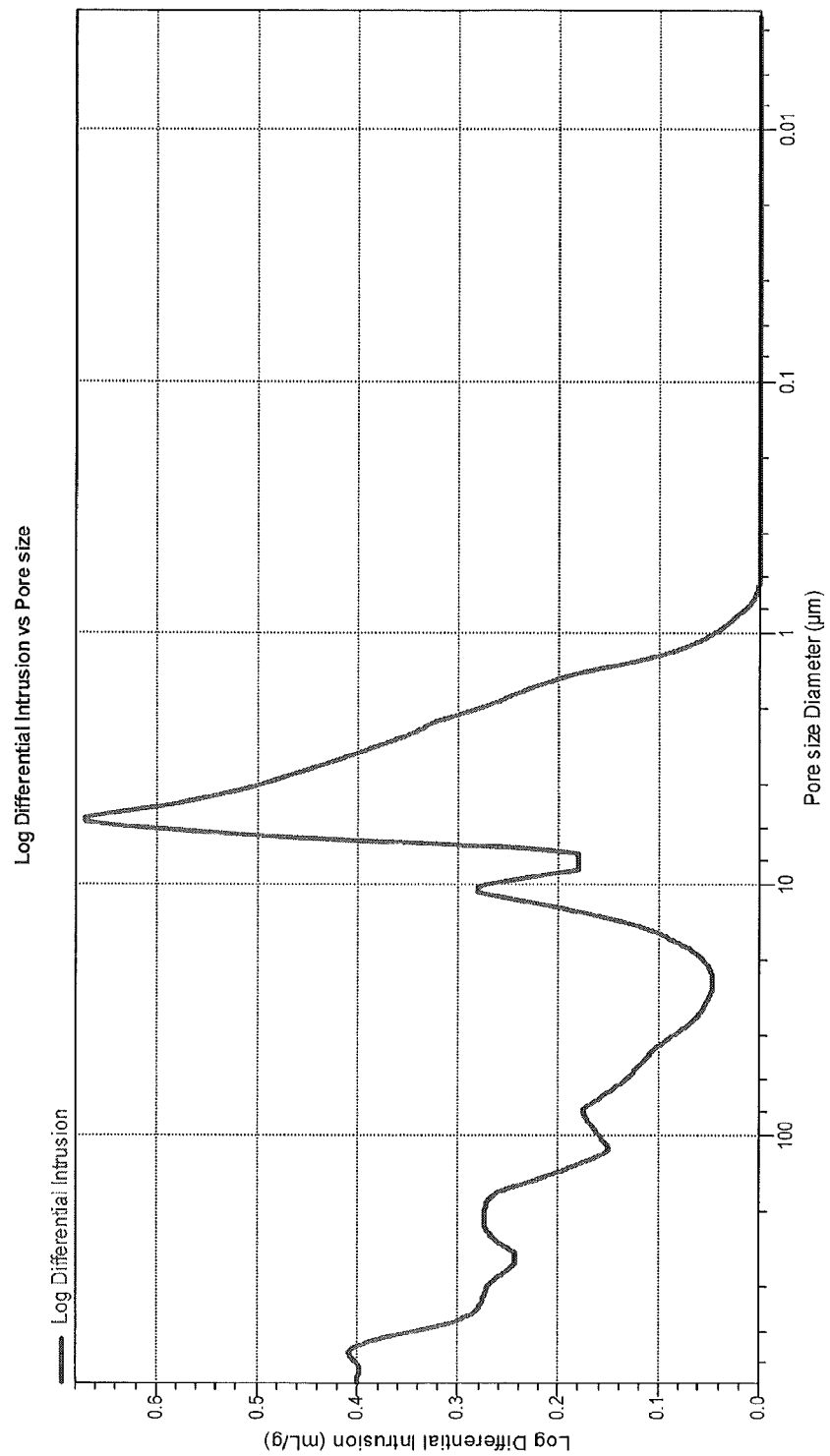

FIG. 4 shows the differential intrusion of the sintered sample, i.e. the inorganic body according to Example 4 as a function of the pore size, as determined via mercury intrusion porosimetry according to DIN 66133. On the x axis, the pore size is shown in micrometer. On the y-axis, the differential intrusion is shown (logarithmic scale).

Figure 5:
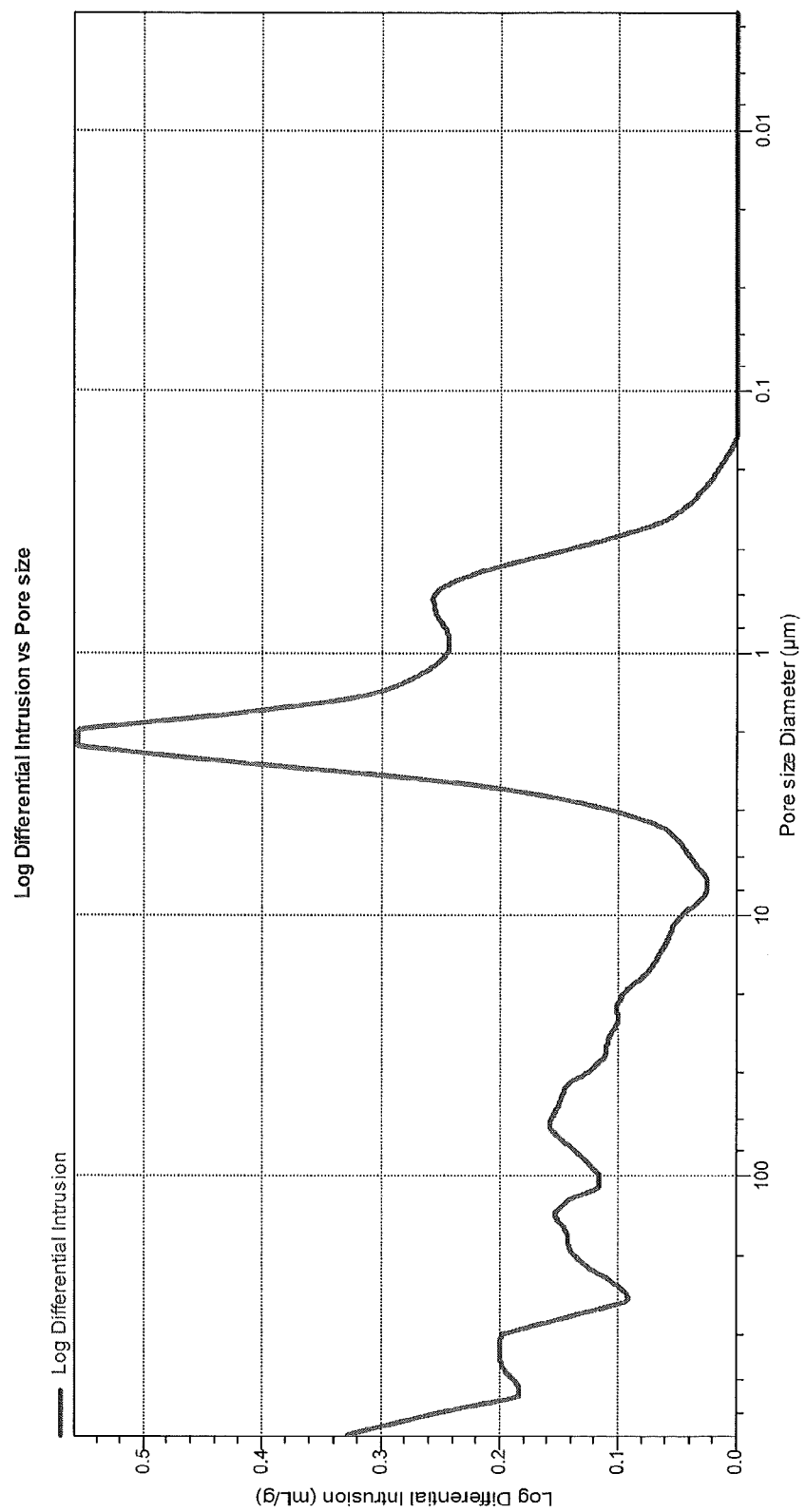

FIG. 5 shows the differential intrusion of the sintered sample, i.e. the inorganic body according to Example 5 as a function of the pore size, as determined via mercury intrusion porosimetry according to DIN 66133. On the x axis, the pore size is shown in micrometer. On the y-axis, the differential intrusion is shown (logarithmic scale).

FIG. 6 symbolically depicts an embodiment of the inventive extruder 10 in continuous lines and auxiliary components in dashed lines. The extruder 10 is separated into individual temperature controlled zones 20-28. Each zone comprises an individual electric heater (not depicted) circumferentially enclosing a barrel 30 of the extruder 10. The zones 20-28 are sequenced along the longitudinal axis of the extruder 10 in a direction towards a die head 40 of the extruder 10. Preferably, the zones are adapted and controlled to provide temperatures increasing towards the die head 40. The extruder 10 further comprises an inorganic powder inlet port 50 allowing access to the inside of the barrel 30 in order to introduce inorganic powder 60 into the extruder. The extruder 10 further comprises an optional plasticizing agent inlet port 52 located at about the same location as the inorganic powder inlet port 50 as seen along the longitudinal axis of the extruder. The optional plasticizing agent inlet port 52 is adapted for introducing a blowing agent 62 onto the inside of the extruder. The optional plasticizing agent inlet port 52 and the inorganic powder inlet port 50 are located at the same zone 20. The extruder further comprises a binder inlet port 54. The binder inlet port 54 is adapted to forward a liquid solution 64 to the inside of the barrel 30, the solution comprising a binder. The binder inlet port 54 is located downstream the optional plasticizing agent inlet port 52 and the inorganic powder inlet port 50 in a direction along the longitudinal axis of the extruder 10 and towards the die head 40. This direction corresponds to the conveying direction of the extruder. Further ports 56 and 58 are given adapted for introducing optional additives 66, 68 into the extruder. The ports 50-58 extend through the wall of the barrel 30. A modified embodiment not shown in the figures does not comprise the optional plasticizing agent inlet port. In particular in zones adapted for temperatures above the boiling point of liquids to be introduced into the extruder, the ports of the embodiment shown in FIG. 6 are adapted to block any pressure compensation from the inside of the barrel 30 to the surrounding of the extruder 10. Preferably, the section of the barrel 30 above this boiling point, for example 100° C. for water as solvent or dispersion medium, is a continuous cylinder without through holes or ports within the wall of the barrel 30. In the inside of the barrel 30, an extruder screw 70 is provided. The extruder screw can be subdivided in distinct longitudinal sections. Distinct sections may have different leads (not depicted). The extruder screw 70 is adapted for conveying the mixture located in the extruder 10 and for homogenizing the mixture. The extruder screw 70 is driven by an electric drive 80. The electric drive 80 comprising an electric motor and a pertaining control is an auxiliary component for operating the extruder 10 and is mechanically connected to the extruder screw 70. Opposite to the end of the extruder 70 screw at which the electric motor 80 is connected, the die head 40 is located. The die head 40 comprises a nozzle 42, which is attached to an extruder plate 44 of the die head 40. The extruder plate comprises a nozzle feeding channel 48 in the extruder plate 44 and an inner nozzle channel 46 in the nozzle, wherein the nozzle feeding channel 48 and the inner nozzle channel 46 are connected. The nozzle 42 comprises an output side 49 forming circumferential sharp edge with the end of the inner nozzle channel 46 opposite to the extruder plate 44. In FIG. 7, the die head is depicted in further detail. Apart from the electric drive 80 as an auxiliary component, a container 82 (not shown) adapted to contain the inorganic powder 60 can be provided for delivering the inorganic powder 60. Further, a conveying belt 84 is provided downstream the die head 40 for receiving porous inorganic bodies provided by the extruder 10. The conveying belt 84 is equipped with at least one temperature controlled chamber 86. The conveying belt 84 conveys the porous inorganic bodies provided by the extruder 10 along a direction 88 of transportation according to the conveying belt 84.

FIG. 7 shows a die head of the inventive extruder, in particular the die head as depicted in FIG. 6. Similar components are provided with the same reference signs, apart from the leading "1" of the reference signs of FIG. 6. An end section of the barrel 130 is provided abutting to the die head 140. The die head 140 comprises a recess 140a and a nozzle 142 attached to an extruder plate 144 of the die head 140 via a threaded connection 146a. The nozzle 142 comprises an inner nozzle channel 146. The inner nozzle channel 146 is directly connected to a nozzle feeding channel 148 within the extruder plate. The recess 140a comprises an apex through which the longitudinal axis L of the die head 140 extends and to which the nozzle feeding channel 148 abuts to. The nozzle feeding channel 148 is directly connected to the inner nozzle channel 146. The nozzle feeding channel 148 is continued by the inner nozzle channel 146. The nozzle 142 is in direct fluidic connection with the recess 140a via the nozzle feeding channel 148 within the extruder plate 144. The nozzle feeding channel 148 provides an intermediate connection between the inner nozzle channel 146 and the recess 140a. In an alternative embodiment, which is not shown, the inner nozzle channel extends through the extruder plate to the recess. In this case, the inner nozzle channel and in particular the nozzle itself is in direct connection with the recess, without any intermediate connection between nozzle and recess. The nozzle shown in FIG. 7 comprises a circumferential outer surface 142a and a front surface 142b at the output side of the nozzle 142 opposite to the extruder plate 144 from which the nozzle 142 extends. The front surface 142b is in the form of a ring with a width of ca. 0.2 mm. The width of the ring corresponds to the wall width of the nozzle at the front surface 142b. The inner diameter of the nozzle 142, i.e. the diameter of the inner nozzle channel 146, is preferably 2 mm to 8 mm and in particular about 2 mm, about 4 mm, about 6 mm or about 8 mm with a tolerance of ±10%. In an embodiment similar to the embodiment shown in FIG. 7, a central spike (extending along the longitudinal axis of the nozzle) is provided inside the nozzle resulting in an inner nozzle channel having the shape of a hollow cylinder. In a particular embodiment, the inner nozzle channel, the nozzle feeding channel and the recess have a center axis corresponding to the longitudinal axis L of the extruder or are parallel thereto. The inner nozzle channel, the nozzle feeding channel and the recess are radially symmetric to the longitudinal axis L. Further, the inner nozzle channel and the nozzle feeding channel can be arranged on the same longitudinal axis. In another embodiment, the axis of the inner nozzle channel and/or the axis of the nozzle feeding channel is parallel to the axis of the recess with a radial displacement >0. In addition, the axis of the inner nozzle channel and the axis of the nozzle feeding channel is radially displaced by a displacement >0. The nozzle feeding channel and/or the inner nozzle channel can extend along a straight line parallel or along or inclined to the longitudinal axis of an extruder screw of the extruder. Further, the nozzle feeding channel and/or the inner nozzle channel can extend along a bent line. The nozzle feeding channel is in fluidic connection to the inner nozzle channel. The extruder further comprises at least one and preferably two extruder screws 170 (one of which is shown in FIG. 7) within a barrel 130 the respective ends of which are shown in FIG. 7. The extruder screw 170 has a flat or rounded apex 172. A tapered end of the extruder screw 170 extends within the recess 140a within the extruder plate 144 of the die head 140. A dead space 149 is provided between the extruder screw 170, in particular its apex 172, and a section of the extruder plate 144 forming the recess. The apex 172 of the extruder screw 170 shown in FIG. 6 and the apex of the recess both lie on the longitudinal axis of the extruder screw 170. Preferably, this applies to all extruder screws and apices of corresponding recesses, including the screw(s) and recess(es) not shown in FIG. 7. The apex of the recess 140a is located at a point of the extruder plate 144 at which the extruder plate has the smallest width. From the apex of the recess 140a, the nozzle feeding channel 148 extends towards the nozzle 142. Alternatively, the inner nozzle channel extends from the apex of the recess in case that the nozzle and the inner nozzle channel directly abuts to the recess 140a and the dead space 149. In a particular embodiment, the extruder screw 170 has an outer thread (not shown) extending into the recess 140a in order to convey the mixture to the dead space. The extruder plate 144 comprises a cooling channel 140a extending from outside of the die head 140 to a cavity 140b within the extruder plate 144. The cavity 140b surrounds a central section of the extruder plate 144 in which the dead volume 149 of ca. 12000 mm$^2$ corresponding to 12 ml is located. The channel 144a is adapted to provide a fluidic connection to the cavity 140b in order to supply and remove a heat transfer medium, preferably in a continuous way, enabling temperature control of the die head. The dead volume 149 as well as the recess 140a has no direct fluidic connection to the cavity 140b and the channels 144a. A flange connection 144c comprising screws is provided attaching the extruder plate (and the die head) to the end face of the barrel 130. Any opening of the flange connection 144c is separated from the channels 144a, in particular by a distance in the direction perpendicular to the plane of projection of FIG. 7.

FIG. 8 shows a first embodiment of a nozzle of the inventive extruder. In FIG. 8, a nozzle is shown, which is attached to an extruder plate 244. The extruder plate 244 of the inventive extruder is shown only in part and symbolically. The extruder plate 244 is a part of a die head of the inventive extruder. The nozzle comprises a first section in form of a hollow cylinder as well as a second section in form of a hollow cone. The first and second sections are longitudinal sections of the nozzle and directly abut each other. The second section is located downstream the first section. The nozzle comprises an outer thread, which is connected to an inner thread of the extruder plate 244, both threads forming a threaded connection 246a. The outer thread of the nozzle is provided circumferentially at an end of the nozzle opposite to an output end of the nozzle. The extruder plate 244 comprises a nozzle feeding channel 248. The inner surface of the nozzle forms an inner nozzle channel 246, which is in direct connection with the nozzle feeding channel 248. Thus, the extrudate provided by the extruder is directed through the nozzle feeding channel 248 and the inner nozzle channel 246 along arrow 249. The nozzle shown in FIG. 8 further comprises an outer surface 242a which is tapered along the direction provided by arrow 249, i.e. along the direction of the extension of the nozzle and towards the output end of the nozzle. A front surface 242b is provided at the output end of the nozzle, which is located opposite to the threaded connection 246a and the nozzle plate 244. The front surface 242b of the nozzle is in form of a ring with a thickness of S. The inner nozzle channel 246 has a diameter D. The nozzle has a length L between the front surface 242b and a front face of the extruder plate 244 from which the nozzle extends. The length L denotes the dimension by which the nozzle protrudes from the nozzle plate. A part of the nozzle, in particular the part surrounded by the threaded connection 246a, extends into the extruder plate. Therefore, L is not the complete length of the nozzle but is the length of the nozzle with which the nozzle extends from the extruder plate. The inner channel 246 of the nozzle has a cross section in form of a full circle of diameter D. The inner cross section of the inner nozzle channel 246 has a constant cross section along the complete length of the nozzle. The thickness of the ring formed by the front surface 242b of the nozzle, which can also be denoted as wall width S, is 1 mm at most, preferably 0.5 mm at most and more preferably 0.25 mm at most. In a particular example, S is 0.2 mm. In the example shown in FIG. 8, the front surface 242b and/or the circumferential outer surface 242a is polished or is an otherwise smoothed surface. Diameter D is preferably less than 5 mm, and is preferably 4 mm or, most preferably, 2 mm. L is preferably less 30 mm at most, 20 mm at most, or 10 mm at most. In an example, L is about 20 mm or, alternatively, 30 mm. Regarding FIG. 8, the dimensions are given with a tolerance of ±10%.

In FIG. 9, a further, second embodiment of a nozzle of the inventive extruder is shown. The nozzle is connected to an extruder plate 344 of the extruder via a threaded connection, similar to the threaded connection 246a of FIG. 8. Like the nozzle in FIG. 8, the nozzle of FIG. 9 comprises a first section in form of a hollow cylinder and a second section in form of a hollow cone. The second section, which is directly abutting to the first section, downstream the first section, comprises a circumferential outer surface 342a which is tapered towards the output end of the nozzle. At the output side of the nozzle, a front surface of the nozzle is provided in form of a ring with a thickness of S, which is also denoted as wall thickness at the output side of the nozzle. In contrast to the inner channel 246 of the FIG. 8, the inner channel of the nozzle of FIG. 9 is in form of a hollow cylinder and has an inner cross section in form of a ring (in contrast to the inner cross section of the nozzle of FIG. 8, which is in form of a full circle). A spike 380 coextends along the longitudinal axis of the nozzle limiting the inner channel 346 of the nozzle of FIG. 9 to a hollow cylinder. The spike 380 is located in the center axis of the nozzle. The arrows 349', 349 show the direction in which the extrudate is directed through the nozzle. The spike 380 is attached to a base 382, which is inserted in the nozzle, in particular in the first section of the nozzle. In order to allow extrudate flowing through the base 382, the base comprises openings extending through the base and along an axial direction of the nozzle. In particular, the base 382 is in form of a ring, which is fully or partly inserted into the inner surface of the nozzle (at the first section of the nozzle). In particular, an outer rim of the base is inserted into the body of the nozzle. The ring has a bar to which the spike 380 is attached to. The bar extends diametrically through the ring of the base 382. The base 382, i.e. the ring including the bar, extends perpendicular to the spike 380. As can be seen when comparing arrows 349 and 349' reflecting the flow of extrudate through the nozzle, the flow provided through the nozzle feeding channel 348 within the nozzle plate 344 has a cross section in form of a full circle, wherein, downstream the base 382, the stream has a cross section in form of a ring since the spike 380 fills out a centered circular cross section of the inner nozzle channel. The spike 380 protrudes from the output side of the nozzle by a length X and the spike has a circular cross section with a diameter Y which is constant along the length of the spike. The inner surface of the nozzle, i.e. the outer surface of the inner nozzle channel 346, has an outer diameter D. The inner diameter of the inner nozzle channel 346 corresponds to the diameter of the spike 380 and is Y. The nozzle is partly inserted into the nozzle plate 344 (by the complete length of the threaded connection 346a) and protrudes the extruder plate by a length L. Thus, the dimensions D, S and L are comparable with the corresponding dimensions shown in FIG. 8. L is preferably 30 mm at most, more preferably 20 mm at most, and most preferably 10 mm at most. D is preferably less than 10 mm and preferably 8 mm at most. The term D-Y (corresponding to an equivalent open diameter of the inner nozzle channel) is preferably 8 mm at most, more preferably 6 mm at most and most preferably 5 mm at most. The nozzle of FIG. 9 provided with an inner spike 380 allows an increased homogeneity due to the mixing properties of the spike 380 and the base 382. In an example, L is about 10 mm±10%, D is 8 mm±10%, X is 1.5 mm 10%, Y is 3 mm±10% an the term D-Y is 5 mm±10%. Only one or a subcombination of these dimensions can apply for an embodiment of the invention. In a modified embodiment, a nozzle is provided as shown in FIG. 9 apart from X being 0 such that the spike does not protrude the output end of the nozzle. Further, the front surface at the output side of the nozzle and/or the circumferential surface 342a is preferably a smoothed surface, for example a polished surface. The nozzles of the extruder and in particular the nozzles shown in FIGS. 6-9 can be provided as polished metal elements. In particular, the nozzles can be attached to the die plate by a threaded connection. The threaded connection can be provided with a sealing, for example a sealing ring, which sealingly connects the nozzle(s) and the die plate. Alternatively, the threaded connection can be provided without sealing, wherein the nozzle and the die plate are in direct connection providing a fluidic connection.

FIGS. 8 and 9 are not drawn to scale. In particular, the extruder plate and the threaded connection are drawn symbolically only. In addition, explicit values for the dimensions of the inventive nozzles shown in FIGS. 8 and 9 are given in Reference Example 2.

In the following, embodiments of the inventive extruder are given, followed by method steps pertaining to the intermediate body and the calcined green body. In addition, examples 1-9 and reference examples 1-2 are given. The present invention also relates to the following embodiments 1 to 10 including the combination of embodiments resulting from the individual back-references in embodiments 2 to 10:

1. A zoned temperature-controllable extruder comprising a die head, at least one extruder screw, a barrel in which the at least one extruder screw extends, and at least two zones including a first zone and a second zone provided downstream the first zone, the extruder further comprising an inorganic powder inlet port and a binder inlet port located downstream the inorganic powder inlet port, wherein a dead volume between an end of the extruder screw is provided, the ratio of the dead volume and an inner radius of the barrel being at most 2000 mm², wherein the die head further comprises at least one nozzle feeding channel extending from the dead volume and at least one nozzle with an inner nozzle channel directly connected to the nozzle feeding channel, and wherein the inner nozzle channel of the at least one nozzle has an inner channel with an angled ending.
2. The extruder according to embodiment 1, wherein the die head comprises an extruder plate having at least one recess into which the end of the extruder screw extends at least partly.
3. The extruder according to embodiment 1 or 2, wherein at an output side of the nozzle, the nozzle is provided with a wall width of 1 mm at most, preferably 0.5 mm at most, more preferably 0.25 mm at most.
4. The extruder according to any of embodiments 1 to 3, wherein the distance between the extruder screw and the nozzle at most 20 mm+/−10%, preferably at most 15 mm+/−10%, more preferably at most 12 mm+/−10%, more preferably at most 10 mm+/−10%.
5. The extruder according to any of embodiments 1 to 4, wherein the inner nozzle channel directly connected to the nozzle feeding channel together have a total channel length of at most 60 mm at most, preferably at most 50 mm, more preferably at most 40 mm.
6. The extruder according to any of embodiments 1 to 5, wherein the at least one nozzle has a smoothened front surface at the output side and/or a smoothened circumferential outer surface at the output side.
7. The extruder according to any of embodiments 1 to 6, wherein the die head further comprises a cooling channel, in particular in connection with an inner chamber within the die head.
8. The extruder according to any of embodiments 1 to 7, wherein the extruder comprises two extruder screws in parallel thus forming a double-screw extruder, both screws being located in the barrel.
9. Use of an extruder according to any of embodiments 1 to 8 for the preparation of an inorganic body, preferably for the preparation of an inorganic body as defined hereinabove.
10. A process for the preparation of an inorganic body, preferably for the preparation of an inorganic body as defined hereinabove, wherein an extruder according to any of embodiments 1 to 8 is employed.

Step f)

According to optional step f) of the process, the intermediate body obtained from step e) is subjected to a temperature of from 100° C. to 120° C. wherein remaining water is removed from the intermediate body. Said subjecting to a temperature of from 100° C. to 120° C. can be carried out in all suitable atmospheres, with air, lean air or technical nitrogen being preferred, with air being more preferred. From step f), a green body is obtained.

Step g)

According to step g) of the process, the intermediate body, or, in case step f) has been carried out, the green body, is calcined at a temperature of from 300 to 1100° C., preferably from 500 to 1000° C., more preferably from 700 to 900° C. The calcination is performed for a time preferably in the range of from 1 to 24 h, more preferably from 2 to 12 h, more preferably from 3 to 6 h. Said calcination can be carried out in all suitable atmospheres, with air, lean air or technical nitrogen being preferred, with air being more preferred. From step g), the calcined green body is obtained.

Step h)

According to optional step g) of the process, the calcined green body is sintered at a temperature higher than the calcination temperature up to at most 2000° C., preferably of from 1000 to 1900° C., more preferably from 1100 to 1800° C., more preferably from 1200 to 1600° C., more preferably from 1300 to 1500° C. The sintering is performed for a time preferably in the range of from 1 to 24 h, more preferably from 2 to 12 h, more preferably from 3 to 6 h. Said sintering can be carried out in all suitable atmospheres, with air, lean air or technical nitrogen being preferred, with air being more preferred. From step h), the porous inorganic body is obtained.

According to an especially preferred embodiment of the present invention, step h) is carried out.

Thus, the present invention also relates to an inorganic body as obtainable or obtained by a process as defined above, said process most preferably comprising step h).

The present invention includes the following embodiments, wherein these include the specific combinations of embodiments as indicated by the respective interdependencies defined therein:

11. A porous inorganic body comprising pores A having a pore size $S_A$ in the range of from 0.005 to 20 micrometer and a total pore volume $V_A$, and comprising pores B having a pore size $S_B$ in the range of from more than 20 to 1000 micrometer and a total pore volume $V_B$, wherein the total pore volume of the pores having a pore size in the range of from 0.005 to 1000 micrometer is $V_C$ and wherein the ratio $R_A=V_A/V_C$ is in the range of from 0.3 to 0.7 as determined via mercury intrusion porosimetry according to DIN 66133.
12. The inorganic body where $R_A$ is in the range of from 0.35 to 0.65.
13. The inorganic body where $S_A$ is in the range of from 0.1 to 20 micrometer and $S_B$ is in the range of from 100 to 1000 micrometer.
14. The inorganic body where $S_A$ is in the range of from 0.4 to 20 micrometer.
15. The inorganic body of where the differential intrusion determined via mercury intrusion porosimetry according to DIN 66133 as a function of the pore size contains at least one peak in the pore size range of from 0.005 to 20 micrometer and at least one peak in the pore size range of from 20 to 1000 micrometer.
16. The inorganic body having a specific surface area (BET) as determined according to DIN ISO 9277 in the range of from 0.5 to 1.5 m$^2$/g, preferably of from 0.8 to 1.2 m$^2$/g.
17. The inorganic body having a water absorption in the range of from 0.4 to 1.5 ml/g, preferably of from 0.5 to 1.0 ml/g, as determined according to Reference Example 1.
18. The inorganic body with at least 95 weight-% thereof, preferably at least 99 weight-% thereof being comprised of alumina, preferably alpha alumina.
19. The inorganic body comprising at least one element selected from the group consisting of alkali metals, alkaline earth metals, silicon, and iron, preferably selected from the group consisting of sodium, silicon, and iron.
20. The inorganic body comprising of from 200 to 750 weight-ppm of sodium, up to 600 weight-ppm, preferably of from 350 to 550 weight-ppm of silicon, and up to 100 weight-ppm of iron, based on the total weight of the inorganic body, calculated as element and as determined via elemental analysis.
21. The inorganic body having the geometry of a cylinder, preferably having a length in the range of from 3 to 20 mm, preferably of from 5 to 10 mm, an outer diameter in the range of from 2 to 20 mm, preferably of from 5 to 10 mm, and a ratio of outer diameter (in mm) relative to wall thickness (in mm) in the range of from 1 to 15, preferably of from 2.5 to 4.5.
22. The inorganic body of for use as a catalyst carrier or as a catalyst, preferably as a catalyst carrier of a silver based catalyst for the preparation of ethylene oxide.
23. A process for the preparation of a porous inorganic body, preferably of a porous inorganic body according to embodiments 11 to 22, said process comprising
    a) supplying a sinterable inorganic powder, preferably an alumina powder, more preferably an alpha alumina powder, at a first zone of a temperature-controllable zoned extruder comprising a die head and at least 3 zones;
    b) supplying an aqueous solution comprising a binder or an aqueous suspension comprising a binder at a second zone of the zoned extruder downstream of the first zone;
    c) mixing the sinterable inorganic powder and the aqueous solution or suspension in the extruder to yield a mixture;
    d) heating the mixture in the zoned extruder up to a temperature of at most 200° C. at an essentially constant volume, thereby increasing the pressure and at least partially vaporizing the water comprised in the mixture to yield a pressurized mixture;
    e) expanding the pressurized mixture into a volume which is at a pressure lower than that of the pressurized mixture to yield a non-flowable intermediate body after extrusion via the die head;
    f) optionally subjecting the intermediate body to a temperature of from 100° C. to 120° C. thereby removing remaining water from the intermediate body to yield a green body;
    g) calcining the green body or the intermediate body at a temperature of from 300° C. to 1100° C.;
    h) optionally sintering the calcined green body at a temperature higher than the calcination temperature up to at most 2000° C. to yield the porous inorganic body;
    wherein said process is preferably a continuous process.
24. The process of embodiment 23 where prior to step d), preferably prior to step c), at least one plasticizing agent is added.
25. The process of embodiment 23 or 24 where prior to step d), at least one pore-forming agent and/or at least one pore forming agent precursor is added.
26. The process of any one embodiment 23 to 25 where prior to step d), preferably in step b), at least one surface active compound and/or at least one blowing agent precursor is added, preferably via the aqueous solution supplied in step b).
27. The process of any wherein one embodiment 23 to 26 where the mixture heated in step d) comprises from 50 to 90 weight-% of the inorganic powder, relative to the total weight of the mixture.
28. The process of embodiment 27 where the mixture heated in step d) comprises, relative to the inorganic powder, from 2 to 20% weight-% of the at least one binder, from 0.5 to 40 weight-% of the at least one plasticizing agent, optionally from 1 to 50 weight-% of the at least one pore-forming agent, optionally from 0.5 to 10 weight-% of the at least one surface active compound, and optionally from 20 to 90 weight-% of the at least one blowing agent precursor.
29. The process of any one embodiment 23 to 28 where the temperature of the mixtures in the extruder zones prior to step d) is below 100° C., preferably at most 95° C., more preferably at most 90° C.
30. The process of any one embodiment 23 to 29 where the temperature-controllable zoned extruder is configured as a double-screw extruder.
31. The process of any one embodiment 23 to 30 where the dead volume of the die head of the temperature-controllable zoned extruder is at most 25 ml, more preferably at most 15 ml, more preferably in the range of from 5 to 15 ml.
32. The process of any one embodiment 23 to 31 where the die head of the temperature-controllable zoned extruder is equipped with a nozzle having an output side and wherein the nozzle has a wall width at the output side of at most 1 mm, preferably at most 0.5 mm, and most preferably at most 0.25 mm.
33. An inorganic body as obtainable or obtained by a process according to any one embodiment of 23 to 32.
34. Use of an inorganic body according to any one embodiment of 11 to 22 or 33 as a catalyst carrier, preferably as a carrier of a catalyst for the preparation of ethylene oxide, more preferably as a carrier of a silver based catalyst for the preparation of ethylene oxide.
35. Method of using an inorganic body according to any one embodiment of 11 to 22 or 33 as a catalyst carrier, preferably as a carrier of a catalyst for the preparation of ethylene oxide, more preferably as a carrier of a silver based catalyst for the preparation of ethylene oxide.

The present invention is further illustrated by the following examples, comparative examples, and reference examples.

EXAMPLES

Example 1

Preparation of an Inorganic Body A

The preparation was carried out using a double-screw extruder according to Reference Example 2. The following process parameters were used
  As ceramic powder, alumina CT 3000 SG (Almatis), having a d50 value of about 0.5-1.5 micrometer, was introduced into zone 1 of the extruder in an amount of 2.7 kg/h.
  As binder, Luviskol® K90 (BASF SE; a polymer based on polyvinylpyrrolidone) was introduced into zone 2 of the extruder. The binder was introduced together with Lutensol® AT 18 (BASF SE; a surfactant based on ethoxylated alcohols) as a surface active compound. Luviskol® K90 (BASF SE) and Lutensol® AT 18 (BASF SE) were introduced in the form of an aqueous solution having the composition 12.8 weight-% Luviskol® K90, 3.2 weight-% Lutensol® AT 18, and 84 weight-% $H_2O$. The aqueous solution was added in an amount of 2.4 kg/h.
  As pore forming agent and as plasticizing agent, graphite (Kropfmühl AG), having a d50 value of about 40 micrometer, was introduced into zone 4 of the extruder in an amount of 0.9 kg/h.
  As plasticizing agent, sodium free (<0.5% Na) Methocel® F4M (Dowwolff Cellulosics) with a viscosity grade of 4000 mPa s was introduced into zone 1 of the extruder in an amount of 0.8 kg/h.
  The screw rotation of the extruder was 300 r.p.m. (rounds per minute).
  The nozzle of the extruder was an 8×3 mm ring nozzle with sharp edges (B-3: see Reference Example 2).
  The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./° C. | 41 | 60 | 70 | 90 | 100 | 110 | 115 | 135 | 115 |

It was found that the continuous process according to the present invention wherein the binder, in the form of an aqueous solution, was added in a zone downstream of the zone in which the ceramic powder is added, ran very smoothly, without inhomogeneous and sudden splitting of the extruding mass, without blockage or narrowing of the extruder nozzle, and only negligible accumulation of the dry slurry occurs at the outer sides of the extruder nozzle.

After calcination of the sample at 800° C. for 5 h in air, it had the following pore size distribution as determined according to mercury intrusion porosimetry according to DIN 66133.

| pore sizes/ micrometer | pore volume | % of total pore volume |
|---|---|---|
| 0.005-1000 | 1.151 | 100 |
| 0.01-0.4 | 0.194 | 17 |
| 0.4-4 | 0.200 | 17 |
| 0.4-10 | 0.426 | 37 |
| 0.4-20 | 0.488 | 42 |
| 10-1000 | 0.531 | 46 |
| 10-300 | 0.347 | 30 |
| 20-1000 | 0.470 | 41 |
| 20-300 | 0.285 | 25 |
| 50-1000 | 0.398 | 35 |
| 50-300 | 0.213 | 19 |
| 100-1000 | 0.318 | 28 |
| 100-300 | 0.133 | 12 |

The main maxima were found at pore sizes of 700, 400, 6.6, and 0.16 micrometer. The water absorption of the calcined sample as determined according to the method as described in Reference Example 1 was 1.15 ml/g.

The sample was further sintered at 1425° C. for 4 h in air at a heating rate of 150 K/hour. The specific surface area (BET) as determined according to DIN ISO 9277 of the sintered sample was 0.9 m$^2$/g. The sample contained 700 ppm Na as determined by elemental analysis. The sintered sample, i.e. the inorganic body of the present invention, had the following pore size distribution as determined according to mercury intrusion porosimetry according to DIN 66133:

| pore sizes/ micrometer | pore volume | % of total pore volume |
|---|---|---|
| 0.005-1000 | 0.831 | 100 |
| 0.01-0.4 | 0.035 | 4 |
| 0.4-4 | 0.199 | 24 |
| 0.4-10 | 0.276 | 33 |
| 0.4-20 | 0.297 | 36 |
| 10-1000 | 0.521 | 63 |
| 10-300 | 0.204 | 25 |
| 20-1000 | 0.500 | 60 |
| 20-300 | 0.183 | 22 |
| 50-1000 | 0.4434 | 53 |
| 50-300 | 0.127 | 15 |
| 100-1000 | 0.390 | 47 |
| 100-300 | 0.073 | 9 |

The main maxima were found at pore sizes of 800, 400, 4, and 0.2 micrometer, as shown in FIG. 1. The water absorption of the sintered sample as determined according to the method as described in Reference Example 1 was 0.69 ml/g.

Example 2

Preparation of an Inorganic Body B

The preparation was carried out using a double-screw extruder according to Reference Example 2. The following process parameters were used:

As ceramic powder, alumina (Almatis), having a d50 value of about 1.5-2 micrometer and a BET surface area of about 5 $m^2/g$ was introduced into zone 1 of the extruder in an amount of 2.7 kg/h.

As binder, Luviskol® K90 (BASF SE; a polymer based on polyvinylpyrrolidone) was introduced into zone 2 of the extruder. The binder was introduced together with Lutensol® AT 18 (BASF SE; a surfactant based on ethoxylated alcohols) as a surface active compound. Luviskol® K90 (BASF SE) and Lutensol® AT 18 (BASF SE) were introduced in the form of an aqueous solution having the composition 12.5 weight-% Luviskol® K90, 7.5 weight-% Lutensol® AT 18, and 80 weight-% $H_2O$. The aqueous solution was added in an amount of 2.6 kg/h.

As pore forming agent and as plasticizing agent, graphite (Kropfmühl AG), having a d50 value of about 40 micrometer, was introduced into zone 4 of the extruder in an amount of 0.9 kg/h.

As plasticizing agent, sodium free (<0.5% Na) Methocel® F4M (Dowwolff Cellulosics) with a viscosity grade of 4000 mPa s was introduced into zone 1 of the extruder in an amount of 0.9 kg/h.

The screw rotation of the extruder was 300 r.p.m. (rounds per minute).

The nozzle of the extruder was an 8×3 mm polished at outer and inner surface ring nozzle with sharp edges and a spike (B-1: see Reference Example 2).

The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./° C. | 41 | 61 | 70 | 90 | 100 | 105 | 110 | 120 | 110 |

It was found that the continuous process according to the present invention wherein the binder, in the form of an aqueous solution, was added in a zone downstream of the zone in which the ceramic powder is added, ran very smoothly, without inhomogeneous and sudden splitting of the extruding mass, without blockage or narrowing of the extruder nozzle, and only negligible accumulation of the dry slurry occurs at the outer sides of the extruder nozzle.

After calcination of the sample at 800° C. for 5 h in air, it had the following pore size distribution as determined according to mercury intrusion porosimetry according to DIN 66133.

| pore sizes/ micrometer | pore volume | % of total pore volume |
|---|---|---|
| 0.005-1000 | 0.988 | 100 |
| 0.01-0.4 | 0.045 | 5 |
| 0.4-4 | 0.254 | 26 |
| 0.4-10 | 0.427 | 43 |
| 0.4-20 | 0.577 | 58 |
| 10-1000 | 0.516 | 52 |
| 10-300 | 0.367 | 37 |
| 20-1000 | 0.366 | 37 |
| 20-300 | 0.217 | 22 |
| 50-1000 | 0.298 | 30 |
| 50-300 | 0.149 | 15 |
| 100-1000 | 0.236 | 24 |
| 100-300 | 0.087 | 9 |

The main maxima were found at pore sizes of 400, 10, 6, and 0.4 micrometer. The water absorption of the calcined sample as determined according to the method as described in Reference Example 1 was 1.42 ml/g.

The sample was further sintered at 1425° C. for 4 h in air at a heating rate of 150 K/hour. The specific surface area (BET) as determined according to DIN ISO 9277 of the sintered sample was 1.0 $m^2/g$. The sample contained 300 ppm Na, 500 ppm Si and less than 100 ppm Fe as determined by elemental analysis. The sintered sample, i.e. the inorganic body of the present invention, had the following pore size distribution as determined according to mercury intrusion porosimetry according to DIN 66133:

| pore sizes/ micrometer | pore volume | % of total pore volume |
|---|---|---|
| 0.005-1000 | 0.731 | 100 |
| 0.01-0.4 | 0.023 | 3 |
| 0.4-4 | 0.210 | 29 |
| 0.4-10 | 0.352 | 48 |
| 0.4-20 | 0.407 | 56 |
| 10-1000 | 0.355 | 49 |
| 10-300 | 0.238 | 33 |
| 20-1000 | 0.301 | 41 |
| 20-300 | 0.183 | 25 |
| 50-1000 | 0.253 | 35 |
| 50-300 | 0.136 | 19 |
| 100-1000 | 0.199 | 27 |
| 100-300 | 0.082 | 11 |

The main maxima were found at pore sizes of 800, 400, 4, and 0.2 micrometer, as shown in FIG. 2. The water absorption of the sintered sample as determined according to the method as described in Reference Example 1 was 0.77 ml/g.

Example 3

Preparation of an Inorganic Body C

The preparation was carried out using a double-screw extruder according to Reference Example 2. The following process parameters were used:

As ceramic powder, alumina (Almatis), having a d50 value of about 1.3-2 micrometer and a BET surface area of about 3 $m^2/g$ was introduced into zone 1 of the extruder in an amount of 2.7 kg/h.

As binder, Luviskol® K90 (BASF SE; a polymer based on polyvinylpyrrolidone) was introduced into zone 2 of the extruder. The binder was introduced together with Lutensol® AT 18 (BASF SE; a surfactant based on ethoxylated alcohols) as a surface active compound. Luviskol® K90 (BASF SE) and Lutensol® AT 18 (BASF SE) were introduced in the form of an aqueous solution having the composition 12.8 weight-% Luviskol® K90, 3.2 weight-% Lutensol® AT 18, and 84 weight-% H$_2$O. The aqueous solution was added in an amount of 2.5 kg/h.

As pore forming agent and as plasticizing agent, graphite (Kropfmuhl AG), having a d50 value of about 40 micrometer, was introduced into zone 4 of the extruder in an amount of 0.9 kg/h.

As plasticizing agent, sodium free (<0.5% Na) Methocel® F4M (Dowwolff Cellulosics) with a viscosity grade of 4000 mPa s was introduced into zone 1 of the extruder in an amount of 0.9 kg/h.

The screw rotation of the extruder was 300 r.p.m. (rounds per minute).

The nozzle of the extruder was an 8×3 mm polished at outer and inner surface ring nozzle with sharp edges and a spike (B-1: see Reference Example 2).

The temperature profile in the seven zones of the extruder and the die head were as follows ("TM" refers to the temperature of the ceramic slurry immediately before the die head (upstream the die head)):

|  | Zone |  |  |  |  |  |  | die head | TM |
| --- | --- | --- | --- | --- | --- | --- | --- | --- | --- |
|  | 1 | 2 | 3 | 4 | 5 | 6 | 7 |  |  |
| Temp./° C. | 41 | 60 | 70 | 90 | 100 | 105 | 110 | 118 | 109 |

It was found that the continuous process according to the present invention wherein the binder, in the form of an aqueous solution, was added in a zone downstream of the zone in which the ceramic powder is added, ran very smoothly, without inhomogeneous and sudden splitting of the extruding mass, without blockage or narrowing of the extruder nozzle, and only negligible accumulation of the dry slurry occurs at the outer sides of the extruder nozzle.

After calcination of the sample at 800° C. for 5 h in air, it had the following pore size distribution as determined according to mercury intrusion porosimetry according to DIN 66133.

| pore sizes/ micrometer | pore volume | % of total pore volume |
| --- | --- | --- |
| 0.005-1000 | 1.064 | 100 |
| 0.01-0.4 | 0.039 | 4 |
| 0.4-4 | 0.381 | 36 |
| 0.4-10 | 0.431 | 41 |
| 0.4-20 | 0.537 | 50 |
| 10-1000 | 0.596 | 56 |
| 10-300 | 0.382 | 36 |
| 20-1000 | 0.489 | 46 |
| 20-300 | 0.276 | 26 |
| 50-1000 | 0.317 | 30 |
| 50-300 | 0.103 | 10 |
| 100-1000 | 0.274 | 26 |
| 100-300 | 0.06 | 6 |

The main maxima were found at pore sizes of about 1000, 32, and 0.85 micrometer. The water absorption of the calcined sample as determined according to the method as described in Reference Example 1 was 1.13 ml/g.

The sample was further sintered at 1425° C. for 4 h in air at a heating rate of 150 K/hour. The specific surface area (BET) as determined according to DIN ISO 9277 of the sintered sample was 0.8 m$^2$/g. The sample contained 300 ppm Na, 400 ppm Si and 200 ppm Fe as determined by elemental analysis. The sintered sample, i.e. the inorganic body of the present invention, had the following pore size distribution as determined according to mercury intrusion porosimetry according to DIN 66133:

| pore sizes/ micrometer | pore volume | % of total pore volume |
| --- | --- | --- |
| 0.005-1000 | 0.767 | 100 |
| 0.01-0.4 | 0.007 | 1 |
| 0.4-4 | 0.227 | 30 |
| 0.4-10 | 0.408 | 53 |
| 0.4-20 | 0.434 | 57 |
| 10-1000 | 0.352 | 46 |
| 10-300 | 0.148 | 19 |
| 20-1000 | 0.326 | 43 |
| 20-300 | 0.122 | 16 |
| 50-1000 | 0.313 | 41 |
| 50-300 | 0.109 | 14 |
| 100-1000 | 0.287 | 37 |
| 100-300 | 0.083 | 11 |

The main maxima were found at pore sizes of 750, 350, and 5 micrometer, as shown in FIG. 3. The water absorption of the sintered sample as determined according to the method as described in Reference Example 1 was 0.84 ml/g.

Example 4

Preparation of an Inorganic Body D

The preparation was carried out using a double-screw extruder according to Reference Example 2. The following process parameters were used:

As ceramic powder, alumina (Almatis), having a d50 value of about 1.3-2 micrometer and a BET surface area of about 3 m$^2$/g was introduced into zone 1 of the extruder in an amount of 2.7 kg/h.

As binder, Luviskol® K90 (BASF SE; a polymer based on polyvinylpyrrolidone) was introduced into zone 2 of the extruder. The binder was introduced together with Lutensol® AT 18 (BASF SE; a surfactant based on ethoxylated alcohols) as a surface active compound. Luviskol® K90 (BASF SE) and Lutensol® AT 18 (BASF SE) were introduced in the form of an aqueous solution having the composition 12.5 weight-% Luviskol® K90, 7.5 weight-% Lutensol® AT 18, and 80 weight-% H$_2$O. The aqueous solution was added in an amount of 2.6 kg/h.

As pore forming agent and as plasticizing agent, graphite (Kropfmühl AG), having a d50 value of about 40 micrometer, was introduced into zone 4 of the extruder in an amount of 0.9 kg/h.

As plasticizing agent, sodium free (<0.5% Na) Methocel® F4M (Dowwolff Cellulosics) with a viscosity grade of 4000 mPa s was introduced into zone 1 of the extruder in an amount of 0.9 kg/h.

The screw rotation of the extruder was 300 r.p.m. (rounds per minute).

The nozzle of the extruder was an 8×3 mm polished at outer and inner surface ring nozzle with sharp edges and a spike (B-1: see Reference Example 2).

The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./°C. | 41 | 60 | 70 | 90 | 100 | 105 | 110 | 120 | 110 |

It was found that the continuous process according to the present invention wherein the binder, in the form of an aqueous solution, was added in a zone downstream of the zone in which the ceramic powder is added, ran very smoothly, without inhomogeneous and sudden splitting of the extruding mass, without blockage or narrowing of the extruder nozzle, and only negligible accumulation of the dry slurry occurs at the outer sides of the extruder nozzle.

After calcination of the sample at 800° C. for 5 h in air, it had the following pore size distribution as determined according to mercury intrusion porosimetry according to DIN 66133.

| pore sizes/micrometer | pore volume | % of total pore volume |
|---|---|---|
| 0.005-1000 | 1.067 | 100 |
| 0.01-0.4 | 0.012 | 1 |
| 0.4-4 | 0.361 | 34 |
| 0.4-10 | 0.421 | 39 |
| 0.4-20 | 0.537 | 50 |
| 10-1000 | 0.635 | 60 |
| 10-300 | 0.453 | 42 |
| 20-1000 | 0.519 | 49 |
| 20-300 | 0.337 | 32 |
| 50-1000 | 0.334 | 31 |
| 50-300 | 0.152 | 14 |
| 100-1000 | 0.275 | 26 |
| 100-300 | 0.093 | 9 |

The main maxima were found at pore sizes of about 830, 30, 4.7, and 0.8 micrometer. The water absorption of the calcined sample as determined according to the method as described in Reference Example 1 was 0.75 ml/g.

The sample was further sintered at 1425° C. for 4 h in air at a heating rate of 150 K/hour. The specific surface area (BET) as determined according to DIN ISO 9277 of the sintered sample was 1.1 m²/g. The sample contained 235 ppm Na, 500 ppm Si and less than 100 ppm Fe as determined by elemental analysis. The sintered sample, i.e. the inorganic body of the present invention, had the following pore size distribution as determined according to mercury intrusion porosimetry according to DIN 66133:

| pore sizes/micrometer | pore volume | % of total pore volume |
|---|---|---|
| 0.005-1000 | 0.734 | 100 |
| 0.01-0.4 | 0.000 | 0 |
| 0.4-4 | 0.165 | 22 |
| 0.4-10 | 0.332 | 45 |
| 0.4-20 | 0.382 | 52 |
| 10-1000 | 0.402 | 55 |
| 10-300 | 0.232 | 32 |
| 20-1000 | 0.353 | 48 |
| 20-300 | 0.182 | 25 |
| 50-1000 | 0.326 | 44 |
| 50-300 | 0.156 | 21 |
| 100-1000 | 0.280 | 38 |
| 100-300 | 0.110 | 15 |

The main maxima were found at pore sizes of 750, 200, 10.5, and 5.5 micrometer, as shown in FIG. 4. The water absorption of the sintered sample as determined according to the method as described in Reference Example 1 was 0.90 ml/g.

Example 5

Preparation of an Inorganic Body E

The preparation was carried out using a double-screw extruder according to Reference Example 2. The following process parameters were used:

As ceramic powder, alumina (Almatis), having a d50 value of about 1.3-2 micrometer and a BET surface area of about 3 m²/g, was introduced into zone 1 of the extruder in an amount of 10.5 kg/h.

As binder, Luviskol® K90 (BASF SE; a polymer based on polyvinylpyrrolidone) was introduced into zone 2 of the extruder. The binder was introduced together with Lutensol® AT 18 (BASF SE; a surfactant based on ethoxylated alcohols) as a surface active compound. Luviskol® K90 (BASF SE) and Lutensol® AT 18 (BASF SE) were introduced in the form of an aqueous solution having the composition 12.8 weight-% Luviskol® K90, 3.2 weight-% Lutensol® AT 18, and 84 weight-% H₂O. The aqueous solution was added in an amount of 5.5 kg/h.

As pore forming agent and as plasticizing agent, graphite (Kropfmühl AG), having a d50 value of about 40 micrometer, was introduced into zone 4 of the extruder in an amount of 3.5 kg/h.

As plasticizing agent, sodium free (<0.5% Na) Walocel™ (Dowwolff Cellulosics) with a viscosity grade of 70000 mPa s was introduced into zone 1 of the extruder in an amount of 0.3 kg/h.

The screw rotation of the extruder was 300 r.p.m. (rounds per minute).

The nozzle of the extruder was an 8×3 mm polished at outer and inner surface ring nozzle with sharp edges and a spike (B-1: see Reference Example 2).

The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./°C. | 40 | 60 | 70 | 90 | 100 | 105 | 110 | 95 | 109 |

It was found that the continuous process according to the present invention wherein the binder, in the form of an aqueous solution, was added in a zone downstream of the zone in which the ceramic powder is added, ran very smoothly, without inhomogeneous and sudden splitting of the extruding mass, without blockage or narrowing of the extruder nozzle, and only negligible accumulation of the dry slurry occurs at the outer sides of the extruder nozzle.

After calcination of the sample at 800° C. for 5 h in air, the calcined sample was sintered at 1425° C. for 4 h in air at a heating rate of 150 K/h. The specific surface area (BET) as determined according to DIN ISO 9277 of the sintered sample was 1.2 m²/g. The sample contained 225 ppm Na, 500 ppm Si and 9 ppm Fe as determined by elemental analysis. The sintered sample, i.e. the inorganic body of the present invention, had the following pore size distribution as determined according to mercury intrusion porosimetry according to DIN 66133:

| pore sizes/ micrometer | pore volume | % of total pore volume |
|---|---|---|
| 0.005-1000 | 0.546 | 100 |
| 0.01-0.4 | 0.019 | 3 |
| 0.4-4 | 0.294 | 54 |
| 0.4-10 | 0.309 | 57 |
| 0.4-20 | 0.325 | 60 |
| 10-1000 | 0.218 | 40 |
| 10-300 | 0.134 | 25 |
| 20-1000 | 0.203 | 37 |
| 20-300 | 0.119 | 22 |
| 50-1000 | 0.167 | 31 |
| 50-300 | 0.083 | 15 |
| 100-1000 | 0.134 | 25 |
| 100-300 | 0.05 | 9 |

The main maxima were found at pore sizes of greater than 100, 2, and 0.6 micrometer, as shown in FIG. 5. The water absorption of the sintered sample as determined according to the method as described in Reference Example 1 was 0.5 ml/g.

Example 6

Preparation of Silver Based Catalysts, and Epoxidation Reactions

Example 6.1

Preparation of a Silver Based Catalyst Based on the Inorganic Body A According to Example 1

Using the sintered sample of Example 1 (inorganic body A) as carrier material, a catalyst with a silver loading of 15.2 weight-% and the additional promoters Li (185 weight-ppm), S (12 weight-ppm), Re (300 weight-ppm), W (215 weight-ppm) and Cs (445 weight-ppm) was prepared by using the following procedure:

6.1.1 Preparation of Silver-Complex Solution 550 g silver nitrate were dissolved in 1.5 l of water. This silver nitrate solution was warmed to 40° C. In another beaker 402.62 g of potassium hydroxide solution (47.8%) were diluted by adding 1.29 l water. Subsequently 216.31 g of oxalic acid dihydrate were added and completely dissolved. This solution is also warmed up to 40° C. The potassium oxalate solution is pumped during a time period of 45 min into the silver nitrate solution using a dosing pump. After the addition the suspension si stirred for 1 h at 40° C. The precipitated silver oxalate was filtered off and was washed using distilled water until the conductivity of the wash water was <40 microSiemens/cm. Using this procedure 620 g of silver oxalate with a water content of 20.80% could be isolated.

306 g ethylene diamine were cooled to 10° C. using an ice bath. 245 g water were added in small portions. After water addition 484.7 g of the wet silver oxalate were added in 30 min into the ethylene diamine water mixture. The temperature during the addition was controlled to stay below 30° C. The mixture was stirred over night at room temperature. The dark suspension was clarified by centrifugation. The silver content of the clear solution (28.73%) was determined by refractometry.

The density (1.531 g/ml) was measured by using a 10 ml graduated cylinder.

6.1.2 Preparation of a Solution Comprising Silver and Promotors 63.94 g silver-complex solution, 0.790 g of a lithium nitrate, ammonium sulfate solution (2.85% by weight lithium and 0.21% by weight sulfur), 1.185 g of a tungstic acid, cesium hydroxide solution containing (2% by weight tungsten and 3.5% by weight cesium) and 0.896 g of a ammonium perrhenate solution 4.1% by weight were added into a beaker and stirred for 5 min at room temperature (rt).

6.1.3 Impregnation of the Carrier (Inorganic Body)

100 g of the porous inorganic body A according to Example 1 were filled into a rotary evaporator. The filled rotary evaporator was evacuated to 10 .mbar. After 10 min of pre evacuation the solution, prepared under 6.1.2, was added drop wise during 15 min. Subsequently the impregnated carrier was rotated for additional 15 min under vacuum.

6.1.4 Calcination of the Impregnated Support

After 1 h at room temperature under normal pressure the impregnated carrier was calcined for 12 min at 283° C. under 8.3 m³/h air in a circulating air oven (Company HORO, Typ 129 ALV-SP, Fabr. Nr.: 53270).

Subsequently, the catalyst was crushed to obtain a catalyst powder fraction with a particle size range of from 0.5 to 0.9 mm. 26.5 g of this powder fraction were used for testing the performance of the catalyst in the production of ethylene oxide.

At a standard operation point, (feed composition: 35% ethylene, 7% oxygen, 56.9% methane, 1% carbon dioxide, 0.1% water, with a reactor temperature of 240° C. and a GHSV of 4750 $h^{-1}$, an ethylene oxide selectivity at a workrate of 250 kg EO/($m^3_{Kat}$ h) of 83% was observed as stable performance at a runtime of 200 h.

Example 6.2

Preparation of a Silver Based Catalyst Based on the Inorganic Body C According to Example 3

Using the sintered sample of Example 3 (inorganic body C) as carrier material, a catalyst with a silver loading of 14.9 weight-% and the additional promoters Li (180 weight-ppm), S (13 weight-ppm), Re (300 weight-ppm), W (200 weight-ppm) and Cs (440 weight-ppm) was prepared by using the following procedure:

6.2.1 Silver-Complex Solution (Preparation See 6.1.1)

The silver content of the clear solution (28.83%) was determined by refractometry.

The density (1.533 g/ml) was measured by using a 10 ml graduated cylinder.

6.2.2 Preparation of a Solution Comprising Silver and Promotors 70.09 g silver-complex solution, 0.869 g of a lithium nitrate, ammonium sulfate solution (2.85% by weight lithium and 0.21% by weight sulfur), 1.30 g of a tungstic acid, cesium hydroxide solution containing (2% by weight tungsten and 3.5% by weight cesium) and 0.986 g of a ammonium perrhenate solution 4.1% by weight were added into a beaker and stirred for 5 min at rt.

6.2.3 Impregnation of the Carrier (Inorganic Body)

110 g of the porous inorganic body C were filled into a rotary evaporator. The filled rotary evaporator was evacuated to 10 .mbar. After 10 min of pre-evacuation the solution, prepared under 6.2.2, was added drop wise during 15 min. Subsequently the impregnated carrier was rotated for additional 15 min under vacuum.

6.2.4 Calcination of the Impregnated Support

After 1 h at room temperature under normal pressure the impregnated carrier was calcined for 12 min at 283° C. under 8.3 m³/h air in a circulating air oven (Company HORO, Typ 129 ALV-SP, Fabr. Nr.: 53270).

Subsequently, the catalyst was crushed to obtain a catalyst powder fraction with a particle size range of from 0.5 to 0.9 mm. 21.7 g of this powder fraction were used for testing the performance of the catalyst in the production of ethylene oxide.

At a standard operation point, (feed composition: 35% ethylene, 7% oxygen, 56.9% methane, 1% carbon dioxide, 0.1% water, with a reactor temperature of 240° C. and a GHSV of 4750 h$^{-1}$, an ethylene oxide selectivity at a workrate of 250 kg EO/(m³$_{Kat}$ h) of 84% was observed as stable performance at a runtime of 125 h.

Example 6.3

Preparation of a Silver Based Catalyst Based on the Inorganic Body E According to Example 5

Using the sintered sample of Example 5 (inorganic body E) as carrier material, a catalyst with a silver loading of 14.2 weight-% and the additional promoters Li (170 weight-ppm), S (12 weight-ppm), Re (330 weight-ppm), W (180 weight-ppm) and Cs (660 weight-ppm) was prepared by using the following procedure:

6.3.1 Silver-Complex Solution (Preparation See 6.1.1)

The silver content of the clear solution (28.53%) was determined by refractometry.

The density (1.503 g/ml) was measured by using a 10 ml graduated cylinder.

6.3.2 Preparation of a Solution Comprising Silver and Promotors 77.21 g silver-complex solution, 0.948 g of a lithium nitrate, ammonium sulfate solution (2.85% by weight lithium and 0.21% by weight sulfur), 1.423 g of a tungstic acid, cesium hydroxide solution containing (2% by weight tungsten and 6.5% by weight cesium) and 1.388 g of a ammonium perrhenate solution 4.1% by weight were added into a beaker and stirred for 5 min at room temperature.

6.3.3 Impregnation of the Carrier (Inorganic Body)

120 g of the porous inorganic body E were filled into a rotary evaporator. The filled rotary evaporator was evacuated to 10 mbar. After 10 min of pre-evacuation the solution, prepared under 6.3.2, was added drop wise during 15 min. Subsequently the impregnated carrier was rotated for additional 15 min under vacuum.

6.3.4 Calcination of the Impregnated Support

After 1 h at room temperature under normal pressure the impregnated carrier was calcined for 12 min at 283° C. under 8.3 m³/h air in a circulating air oven (Company HORO, Typ 129 ALV-SP, Fabr. Nr.: 53270).

Subsequently, the catalyst was crushed to obtain a catalyst powder fraction with a particle size range of from 0.5 to 0.9 mm. 25.7 g of this powder fraction were used for testing the performance of the catalyst in the production of ethylene oxide.

At a standard operation point, (feed composition: 35% ethylene, 7% oxygen, 56.9% methane, 1% carbon dioxide, 0.1% water, with a reactor temperature of 241° C. and a GHSV of 4750 h$^{-1}$, an ethylene oxide selectivity at a workrate of 250 kg EO/(m³$_{Kat}$ h) of 85.5% was observed as stable performance at a runtime of 530 h.

Example 7

Influence of the Order of Addition of the Binder

Example 7.1

Reverse Addition (Comparative)

The process was carried out in a similar manner as described in example 1 of EP-A 0 799 810. The extruder was equipped with a ring nozzle having a diameter of 2 mm (A-1: see Reference Example 2) and, alternatively, with a ring nozzle having a diameter of 8 mm (B-1: see Reference Example 2). The dead volume of the extruder plate was about 40 nil.

In zone 3 of the extruder, alumina CT 3000 SG was introduced in an amount of 4.675 kg/h. Upstream of this zone, in zone 1, an aqueous solution of Luviskol K90® as binder and tetrametyhlammonium oleate (as surface active compound) was introduced in an amount of 1.327 kg/h. The aqueous solution comprised 16.4 weight-% Luviskol K90®, 4.5 weight-% tetrametyhlammonium oleate, and 79.1 weight-% water. The temperature profile in the nine zones of the extruder and the die head were as follows:

| | Zone | | | | | | | | | die |
|---|---|---|---|---|---|---|---|---|---|---|
| | 1 | 2 | 3 | 4 | 5 | 6 | 7 | 8 | 9 | head |
| Temp./° C. | 30 | 40 | 60 | 90 | 100 | 105 | 115 | 115 | 120 | — |

It was found that the extrusion process was very unstable and the alumina powder accumulated at the zone where the powder was added. Formation of an alumina crust was observed, leading to dosing problems and inhomogeneous extrusion. The dosage of the alumina powder was interrupted for several minutes. Extrusion with both the 2 mm ring nozzle and the 8 mm ring nozzle proceeded inhomogeneously.

Example 7.2

Addition of the Binder According to the Invention

The process was carried out as Example 7.1 save the reversed dosing of the reagents. In particular, the aqueous solution according to Example 7.1 was added in zone 3 of the extruder whereas the ceramic powder was added in zone 1, i.e. upstream the zone where the aqueous solution was added.

Contrary to Example 7.1 (comparative), no dosing problems, no accumulation, and no crust building were observed. Later in the process, a pressure increase was observed leading to the splitting of the extrudates and blockage of the 2 mm ring nozzle. The same was observed when using the 8 mm ring nozzle.

Example 7.3

Reverse Addition (Comparative) Using an Extruder Plate with a Lower Dead Volume

The process was carried out as described in Example 7.1. However, the extruder was equipped with an extruder plate having a dead volume of 12 ml, compared with the dead volume of 40 ml according to Example 7.1. The die had used was temperature-adjustable.

The temperature profile in the nine zones of the extruder and the die head were as follows:

| | Zone | | | | | | | | | die |
|---|---|---|---|---|---|---|---|---|---|---|
| | 1 | 2 | 3 | 4 | 5 | 6 | 7 | 8 | 9 | head |
| Temp./° C. | — | 30 | 40 | 60 | 90 | 105 | 105 | 120 | 125 | 125 |

As in Example 7.1, it was found that although an extruder plate with a low dead volume was used, the process was very unstable like observed in Example 7.1 due to dosing problems of alumina powder (accumulation/crust formation) at zone 3.

Example 7.4

Addition of the Binder According to the Invention Using an Extruder Plate with a Lower Dead Volume The experiment was carried out as Example 7.3 (comparative) save the reversed order of dosing of the reagents. In particular, the aqueous solution according to Example 7.3 was added in zone 3 of the extruder whereas the ceramic powder was added in zone 1, i.e. upstream the zone where the aqueous solution was added.

As in example 7.2, it was found that no dosing problems, no accumulation, and no crust building were observed, contrary to the results as obtained in (comparative) Examples 7.1 and 7.3. Yet further, the results obtained according to Example 7.2 could be even improved since, although a certain slurry accumulation was observed at the nozzle edges followed by partial blockage of the 8 mm ring nozzle and the 2 mm ring nozzle used, these effects were observed at process run times considerably longer than those of Example 7.2 (about twice as long for the 2 mm ring nozzle and about ten times as long for the 8 mm ring nozzle).

Thus, it is shown that using an extruder plate with a dead volume in the preferred range, outside the ranges known from the prior art, even improves the good results obtained when the inventive order of addition of the reagents is used.

Example 8

Influence of the Order of Addition of the Binder

Example 8.1

Addition of the Binder According to the Invention Using an Extruder Plate with a Lower Dead Volume The preparation was carried out using a double-screw extruder according to Reference Example 2. The dead volume of the extruder plate was about 11 ml and in particular 11 ml. The following process parameters were used:

As ceramic powder, alumina (Almatis), having a d50 value of about 1.3-2 micrometer and a BET surface area of about 3 m²/g was introduced into zone 1 of the extruder in an amount of 10.5 kg/h.

As binder, Luviskol® K90 (BASF SE; a polymer based on polyvinylpyrrolidone) was introduced into zone 2 of the extruder. The binder was introduced together with Lutensol® AT 18 (BASF SE; a surfactant based on ethoxylated alcohols) as a surface active compound. Luviskol® K90 (BASF SE) and Lutensol® AT 18 (BASF SE) were introduced in the form of an aqueous solution having the composition 12.8 weight-% Luviskol® K90, 3.2 weight-% Lutensol® AT 18, and 84 weight-% $H_2O$. The aqueous solution was added in an amount of 5.5 kg/h.

As pore forming agent and as plasticizing agent, graphite (Kropfmühl AG), having a d50 value of about 40 micrometer, was introduced into zone 4 of the extruder in an amount of 3.5 kg/h.

As plasticizing agent, sodium free (<0.5% Na) Walocel™ (Dowwolff Cellulosics) with a viscosity grade of 70000 mPa s was introduced into zone 1 of the extruder in an amount of 0.3 kg/h.

The screw rotation of the extruder was 300 r.p.m. (rounds per minute).

The nozzle of the extruder was an 8×3 mm polished at outer and inner surface ring nozzle with sharp edges and a spike (B-1: see Reference Example 2).

The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./° C. | 39 | 58 | 70 | 90 | 100 | 105 | 113 | 95 | 113 |

It was found that the continuous process according to the present invention wherein the binder, in the form of an aqueous solution, was added in a zone downstream of the zone in which the ceramic powder is added, ran very smoothly, without inhomogeneous and sudden splitting of the extruding mass, without blockage or narrowing of the extruder nozzle, and only negligible accumulation of the dry slurry occurs at the outer sides of the extruder nozzle.

Example 8.2

Reverse Addition (Comparative)

The process was carried out as in Example 8.1 save reversed order of addition of the alumina (here: at zone 2) and the aqueous phase (here: at zone 1). It was found that the extrusion process was very unstable and the alumina powder accumulated at zone. Formation of an alumina crust was observed, leading to dosing problems and inhomogeneous extrusion. The dosage of the alumina powder was interrupted for several minutes. Thus, the results as obtained in Example 7.3 were confirmed.

Example 8.3

Addition of the Binder According to the Invention Using an Extruder Plate with a Higher Dead Volume The preparation was carried out using a double-screw extruder according to Reference Example 2. The dead volume of the extruder plate was about 35 ml. The following process parameters were used:

- As ceramic powder, alumina (Almatis), having a d50 value of about 1.3-2 micrometer and a BET surface area of about 3 m²/g was introduced into zone 1 of the extruder in an amount of 10.5 kg/h.
- As binder, Luviskol® K90 (BASF SE; a polymer based on polyvinylpyrrolidone) was introduced into zone 2 of the extruder. The binder was introduced together with Lutensol® AT 18 (BASF SE; a surfactant based on ethoxylated alcohols) as a surface active compound. Luviskol® K90 (BASF SE) and Lutensol® AT 18 (BASF SE) were introduced in the form of an aqueous solution having the composition 12.8 weight-% Luviskol® K90, 3.2 weight-% Lutensol® AT 18, and 84 weight-% $H_2O$. The aqueous solution was added in an amount of 5.5 kg/h.
- As pore forming agent and as plasticizing agent, graphite (Kropfmühl AG), having a d50 value of about 40 micrometer, was introduced into zone 4 of the extruder in an amount of 3.5 kg/h.
- As plasticizing agent, sodium free (<0.5% Na) Walocel™ (Dowwolff Cellulosics) with a viscosity grade of 70000 mPa s was introduced into zone 1 of the extruder in an amount of 0.3 kg/h.
- The screw rotation of the extruder was 300 r.p.m. (rounds per minute).
- The nozzle of the extruder was an 8×3 mm polished at outer and inner surface ring nozzle with sharp edges and a spike (B-1: see Reference Example 2).
- The temperature profile in the seven zones of the extruder and the die head were as follows ("TM" refers to the temperature of the ceramic slurry immediately before the die head (upstream the die head)):

| | Zone | | | | | | | | die | |
|---|---|---|---|---|---|---|---|---|---|---|
| | 1 | 2 | 3 | 4 | 5 | 6 | 7 | 8 | head | TM |
| Temp./°C. | 39 | 57 | 71 | 95 | 105 | 110 | 115 | 105 | — | 114 |

It was found that the continuous process according to the present invention wherein the binder, in the form of an aqueous solution, was added in a zone downstream of the zone in which the ceramic powder is added, ran very smoothly, without inhomogeneous and sudden splitting of the extruding mass. No dosing problems, no accumulation, and no crust building were observed. Later in the process, after about 15 minutes, the nozzle was slowly blocked. This again shows that using an extruder plate with a dad volume in the preferred range even improves the already advantageous process of the present invention according to which the ceramic powder, the sinterable organic powder, is added to an extruder zone upstream of the zone where the binder is added.

Example 8.4

Reverse Addition (Comparative) Using an Extruder Plate with a Higher Dead Volume The process was carried out as in Example 8.3 save reversed order of addition of the alumina (here: at zone 2) and the aqueous phase (here: at zone 1). It was found that the extrusion process was very unstable and the alumina powder accumulated at zone. Formation of an alumina crust was observed, leading to dosing problems and inhomogeneous extrusion. The dosage of the alumina powder was interrupted for several minutes. Thus, the results as obtained in Example 7.1 were confirmed.

Example 9

Inventive Method Applied to Ceramic Powders Other than Alumina

Example 9.1

Preparation of an Extrudate Based on a Layered Silicate

The preparation was carried out using a double-screw extruder according to Reference Example 2. The following process parameters were used:

- Ceramic powder at zone 1: A mixture of 3 weight-% Collacral® DS6256 (BASF SE, ammonium polyacrylate), 3 weight-% $NH_4HCO_3$ and 94 weight % K10 layered silicate (acid-activated montmorillonite, Sud Chemie) in an amount of 1.5 kg/h
- Plasticizing agent at zone 1: Lutrol® F127 (BASF SE, ethylene oxide-propylene oxide copolymer) in an amount of 0.2 kg/h
- Aqueous binder phase at zone 4: solution of 8.3 weight % Luviskol® K90, 3.2 weight-% Lutensol® AT18; 88.5 weight % $H_2O$ in an amount of 1.7 kg/h
- Screw rotation speed: 120 r.p.m.
- Nozzle: 4 mm with sharp edges (A-4: see Reference Example 2)
- The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./°C. | 41 | 60 | 70 | 80 | 90 | 100 | 110 | 113 | 109 |

It was found that the continuous process according to the present invention wherein the binder, in the form of an aqueous solution, was added in a zone downstream of the zone in which the ceramic powder is added, ran very smoothly, without nozzle blockage.

Example 9.2

Preparation of an Extrudate Based on a Layered Silicate

The preparation was carried out using a double-screw extruder according to Reference Example 2. The following process parameters were used:

- Ceramic powder at zone 1: A mixture of 3 weight-% Collacral® DS6256, 5 weight-% Aerosil® 200 (fumed silica, Evonik) and 92 weight-% K10 layered silicate (acid-activated montmorillonte, Süd Chemie), in an amount of 1.25 kg/h
- Plasticizing agent at zone 1: low sodium (<0.5% Na) Methocel® F4M with a viscosity grade of 4000 mPa s in an amount of 0.1 kg/h Aqueous binder phase at zone 2: solution of 8.3 weight % Luviskol® K90, 3.2 weight-% Lutensol® AT18; 88.5 weight % H$_2$O in an amount of 2.25 kg/h
Screw rotation speed: 120 r.p.m.
Nozzle: 4 mm with sharp edges (A-4: see Reference Example 2)
The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./°C. | 30 | 60 | 70 | 80 | 90 | 100 | 110 | 115 | 111 |

It was found that the continuous process according to the present invention wherein the binder, in the form of an aqueous solution, was added in a zone downstream of the zone in which the ceramic powder is added, ran very smoothly, without nozzle blockage.

Example 9.3

Preparation of an Extrudate Based on Silica

The preparation was carried out using a double-screw extruder according to Reference Example 2. The following process parameters were used:
Ceramic powder at zone 1: silica (powder, BET surface area 168 m$^2$/g) in an amount of 2 kg/h
Ceramic powder at zone 4: silica (powder, BET surface area 168 m$^2$/g) in an amount of 0.5 kg/h
Plasticizing agent at zone 1: low sodium (<0.5% Na) Walocel™ (Dowwolff Cellulosics) with a viscosity grade of 70000 mPa s in an amount of 0.12 kg/h
Aqueous binder phase at zone 2: solution of 5.2 weight % Luviskol® K90, 1.9 weight-% Lutensol® AT18; 92.9 weight ° A) H$_2$O in an amount of 4.1 kg/h
Screw rotation speed: 120 r.p.m.
Nozzle: polished with sharp edges (A-2: see Reference Example 2)
The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./°C. | 40 | 60 | 70 | 90 | 100 | 110 | 125 | 105 | 119 |

It was found that the continuous process according to the present invention wherein the binder, in the form of an aqueous solution, was added in a zone downstream of the zone in which the ceramic powder is added, ran very smoothly, without pulsations, and without nozzle blockage.

Example 9.4

Preparation of an Extrudate Based on Silica

The preparation was carried out using a double-screw extruder according to Reference Example 2. The following process parameters were used:
Ceramic powder at zone 1: silica (powder, BET surface area 168 m$^2$/g) in an amount of 2 kg/h
Ceramic powder at zone 4: silica (powder, BET surface area 168 m$^2$/g) in an amount of 0.5 kg/h
Plasticizing agent at zone 1: low sodium (<0.5% Na) Walocel™ (Dowwolff Cellulosics) with a viscosity grade of 70000 mPa s in an amount of 0.12 kg/h
Aqueous binder phase at zone 2: solution of 5.2 weight % Luviskol® K90, 1.9 weight-% Lutensol® AT18; 92.9 weight % H$_2$O in an amount of 4.1 kg/h
Screw rotation speed: 120 r.p.m.
Nozzle: sharp edges (B-2: see Reference Example 2), polished
The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./°C. | 40 | 60 | 70 | 90 | 100 | 110 | 125 | 105 | 117 |

It was found that the continuous process according to the present invention wherein the binder, in the form of an aqueous solution, was added in a zone downstream of the zone in which the ceramic powder is added, ran very smoothly, without pulsations, and without nozzle blockage.

Example 9.5

Preparation of an Extrudate Based on Kaolin

The preparation was carried out using a double-screw extruder according to Reference Example 2. The following process parameters were used:
Ceramic powder at zone 1: a mixture of 38.5 weight-% Mullit (1200° C. calcined kaolin, composition of the calcined sample 23.4 weight-% Al, 0.16 weight-% Na, 24.4 weight-% Si), 38.5 weight-% Kaolin (non-calcined kaolin, composition 20.1 weight-% Al, 21.3 weight-% Si, 0.13 weight-% Na), and 23 weight-% Pural SB® (Condea) in an amount of 3.0 kg/h
Plasticizing agent at zone 1: low sodium (<0.5% Na) Walocel™ (Dowwolff Cellulosics) with a viscosity grade of 70000 mPa s in an amount of 0.12 kg/h
Aqueous binder phase at zone 2: solution of 7.1 weight % Luviskol® K90, 1.7 weight-% Lutensol® AT18; 91.2 weight % H$_2$O in an amount of 2.3 kg/h
Solution of Ludox® SM30 (colloidal silica, 30 weight-% in water) at zone 4 in an amount of 1.56 kg/h
Screw rotation speed: 120 r.p.m.
Nozzle: sharp edges (B-2: see Reference Example 2), polished
The temperature profile in the seven zones of the extruder and the die head were as follows ("TM" refers to the temperature of the ceramic slurry immediately before the die head (upstream the die head)):

| | Zone | | | | | | | die | |
|---|---|---|---|---|---|---|---|---|---|
| | 1 | 2 | 3 | 4 | 5 | 6 | 7 | head | TM |
| Temp./°C. | 40 | 60 | 70 | 90 | 100 | 110 | 115 | 105 | 112 |

It was found that the continuous process according to the present invention wherein the binder, in the form of an aqueous solution, was added in a zone downstream of the zone in which the ceramic powder is added, ran very smoothly, without pulsations, and without nozzle blockage.

Example 9.6

Preparation of an Extrudate Based on Kaolin

The preparation was carried out using a double-screw extruder according to Reference Example 2. The following process parameters were used:

Ceramic powder at zone 1: a mixture of 36 weight-% Mullit (1200° C. calcined kaolin, composition of the calcined sample 23.4 weight-% Al, 0.16 weight-% Na, 24.4 weight-% Si), 45 weight-% Kaolin (non-calcined kaolin, composition 20.1 weight-% Al, 21.3 weight-% Si, 0.13 weight-% Na), and 19 weight-% Spinel (1038° C. calcined kaolin, composition of the calcined sample 23.2 weight-% Al, 0.16 weight-% Na, 24.3 weight-% Si) in an amount of 2.5 kg/h Plasticizing agent at zone 1: low sodium (<0.5% Na) Walocel™ (Dowwolff Cellulosics) with a viscosity grade of 70000 mPa s in an amount of 0.16 kg/h Aqueous binder phase at zone 2: solution of 5.2 weight % Luviskol® K90, 1.9 weight-% Lutensol® AT18; 92.9 weight % $H_2O$ in an amount of 2.5 kg/h Solution of Ludox® SM30 (colloidal silica, 30 weight-% in water) at zone 4 in an amount of 0.8 kg/h Screw rotation speed: 120 r.p.m.

Nozzle: sharp edges (B-2: see Reference Example 2), polished

The temperature profile in the seven zones of the extruder and the die head were as follows ("TM" refers to the temperature of the ceramic slurry immediately before the die head (upstream the die head)):

|  | Zone |  |  |  |  |  | die |  |
|---|---|---|---|---|---|---|---|---|
| 1 | 2 | 3 | 4 | 5 | 6 | 7 | head | TM |
| Temp./° C. 40 | 60 | 70 | 90 | 100 | 115 | 125 | 100 | 120 |

It was found that the continuous process according to the present invention wherein the binder, in the form of an aqueous solution, was added in a zone downstream of the zone in which the ceramic powder is added, ran very smoothly, without pulsations, and without nozzle blockage.

All examples 9.1 to 9.6 clearly showed that independent of the specific starting materials and the respective amounts used, the inventive order of addition, namely the addition of the binder in a zone downstream of a zone where at least a portion of the sinterable is added, allows for advantageous processes which run smoothly, which avoid the accumulation of material, and which avoid nozzle blockage.

Reference Example 1

Determination of the Water Absorption

The water absorption of the samples was measured by immersing a weighted sample into water, carefully shaking it for 3 min and than removing the sample from the water. The difference between the weights of the wet and initial samples gives the water adsorption capacity of the sample (in ml water per gram of the sample).

Reference Example 2

The Extruder Used

In the examples, an extruder of type ZSK 25 by Coperion GmbH, Germany, has been used (co-rotating twin-screw extruder; diameter D of the screw: D 0 25 mm; length of the extruder: 34 D). The extruder was assembled modularly based on different elements and was designed having different functional zones as indicated in the examples above:

1. Dosage zone for powder compounds: extruder element with overhead dosage opening and, backwards with respect to the conveying direction, an extruder element with a degassing opening; extruder screw with conventional conveying elements (zone 1).
2. Dosage zone for liquid compounds equipped with an opening, sealed with a cover. Through the cover, one or optionally more pipelines are laid. Through the pipelines, liquid compounds can be pumped into the extruder, optionally via a pressure retaining valve. The extruder screws are equipped with mixing and/or kneading elements in order to admix the liquid compounds with the solid which is already in the extruder and to paste the mixture (zone 2).
3. Extruder element with a degassing opening and downstream extruder element with lateral dosage opening, equipped with a twin-screw feeding for the dosage of solid, preferably powder compounds. The extruder screw is equipped with mixing and/or kneading elements in order to admix the solid/powder compounds (zone 3).
4. Downstream of zone 3: closed extruder elements, equipped with conveying and mixing elements, in ordert homogenize and tempering the mixture (zone 4).
5. The die plate was specially produced with an especially low dead volume. The die plate was heatable and coolable, and equipped with a recess for applying of specially produced nozzles (as described below). The nozzles had different diameters and, among others, were designed to extrude hollow strands.

All extruder elements were heatable and coolable independently, thus allowing fo adjusting the respectively desired temperature profile. The feeding of the solid/powder compounds and the liquid compounds was carried out gravimetrically via differential dosing scales.

The nozzles referred to in the Examples above and abbreviated with A-1, A-2, A-4, B-1, B-2, and B-3 have a geometry is indicated in FIGS. 8 and 9, wherein FIG. 8 shows the type A nozzle (without spike), leading to extrudates/samples having the geometry of a filled cylinder, and wherein FIG. 9 shows the type B nozzle with spike leading to extrudates/samples having the geometry of a hollow cylinder.

| nozzle | L/mm | D/mm | X/mm | Y/mm | polished | S/mm |
|---|---|---|---|---|---|---|
| A-1 | 0 | 2 | — | — | no | >1 |
| A-2 | 10 | 4 | — | — | no | >1 |
| A-4 | 30 | 4 | — | — | no | 0.2 |
| B-1 | 10 | 8 | 1.5 | 3 | yes | 0.2 |
| B-2 | 10 | 6 | 1 | 2 | yes | 0.2 |
| B-3 | 10 | 8 | 0 | 3 | no | 0.2 |

The invention claimed is:

1. A porous inorganic body comprising pores A having a pore size $S_A$ in the range of from 0.005 to 20 micrometer and a total pore volume $V_A$, and pores B having a pore size $S_B$ in the range of from more than 20 to 1000 micrometer and a total pore volume $V_B$, wherein the total pore volume of the pores having a pore size in the range of from 0.005 to 1000 micrometer is $V_C$, and wherein a ratio $R_A=V_A/V_C$ is in the range of from 0.3 to 0.7 as determined via mercury intrusion porosimetry according to DIN 66133.

2. The inorganic body of claim 1, wherein $R_A$ is in the range of from 0.35 to 0.65.

3. The inorganic body of claim 1, wherein $S_A$ is in the range of from 0.1 to 20 micrometer and $S_B$ is in the range of from 100 to 1000 micrometer.

4. The inorganic body of claim 1, wherein $S_A$ is in the range of from 0.4 to 20 micrometer.

5. The inorganic body of claim 1, wherein the differential intrusion determined via mercury intrusion porosimetry according to DIN 66133 as a function of the pore size contains at least one peak in the pore size range of from 0.005 to 20 micrometer and at least one peak in the pore size range of from 20 to 1000 micrometer.

6. The inorganic body of claim 1, having a specific surface area (BET) as determined according to DIN ISO 9277 in the range of from 0.5 to 1.5 m$^2$/g.

7. The inorganic body of claim 1, having a specific surface area (BET) as determined according to DIN ISO 9277 in the range of from 0.8 to 1.2 m$^2$/g.

8. The inorganic body of claim 1, having a water absorption in the range of from 0.4 to 1.5 ml/g.

9. The inorganic body of claim 1, at least 95 weight-% thereof being comprised of alumina.

10. The inorganic body of claim 1, at least 99 weight-% thereof being comprised of alpha alumina.

11. The inorganic body of claim 1, comprising at least one element selected from the group consisting of alkali metals, alkaline earth metals, silicon, and iron.

12. The inorganic body of claim 1, comprising of from 200 to 750 weight-ppm of sodium, up to 600 weight-ppm, of silicon, and up to 100 weight-ppm of iron, based on the total weight of the inorganic body, calculated as element and as determined via elemental analysis.

13. The inorganic body of claim 1, having the geometry of a cylinder, having a length in the range of from 3 to 20 mm, an outer diameter in the range of from 2 to 20 mm, and a ratio of outer diameter (in mm) relative to wall thickness (in mm) in the range of from 1 to 15.

14. The inorganic body of claim 1, having the geometry of a cylinder, having a length in the range of from 5 to 10 mm, an outer diameter in the range of from 5 to 10 mm, and a ratio of outer diameter (in mm) relative to wall thickness (in mm) in the range of from 2.5 to 4.5.

15. A catalyst carrier or a catalyst which comprises the inorganic body of claim 1.

16. A process for the preparation of a porous inorganic body of claim 1, said process comprising
  a) supplying a sinterable inorganic powder, preferably an alumina powder, more preferably an alpha alumina powder, at a first zone of a temperature-controllable zoned extruder comprising a die head and at least 3 zones;
  supplying an aqueous solution comprising a binder or an aqueous suspension comprising a binder at a second zone of the zoned extruder downstream of the first zone;
  c) mixing the sinterable inorganic powder and the aqueous solution or suspension in the extruder to yield a mixture;
  d) heating the mixture in the zoned extruder up to a temperature of at most 200° C. at an essentially constant volume, thus increasing the pressure and at least partially vaporizing the water comprised in the mixture to yield a pressurized mixture;
  e) expanding the pressurized mixture into a volume which is at a pressure lower than that of the pressurized mixture to yield a non-flowable intermediate body after extrusion via the die head;
  f) optionally, subjecting the intermediate body to a temperature of from 100° C. to 120° C. to remove remaining water from the intermediate body to yield a green body;
  g) calcining the green body or the intermediate body at a temperature of from 300° C. to 1100° C.;
  h) optionally, sintering the calcined green body at a temperature higher than the calcination temperature up to at most 2000° C. to yield the porous inorganic body;
  wherein said process is preferably a continuous process.

17. The process of claim 16, wherein the temperature of the mixtures in the extruder zones prior to step d) is below 100° C.

18. The process of claim 16, wherein the temperature-controllable zoned extruder is configured as a double-screw extruder.

19. The process of claim 16, wherein the dead volume of the die head of the temperature-controllable zoned extruder is at most 25 ml.

20. The process of claim 16, wherein the die head of the temperature-controllable zoned extruder is equipped with a nozzle having an output side and wherein the nozzle has a wall width at the output side of at most 1 mm.

21. The process of claim 16, wherein prior to step d), and prior to step c), at least one plasticizing agent is added.

22. The process of claim 16, wherein prior to step d), at least one pore-forming agent and/or at least one pore forming agent precursor is added.

23. The process of claim 16, wherein prior to step d), at least one surface active compound and/or at least one blowing agent precursor is added.

24. The process of claim 16, wherein the mixture heated in step d) comprises from 50 to 90 weight-% of the inorganic powder, relative to the total weight of the mixture.

25. The process of claim 24, wherein the mixture heated in step d) comprises, relative to the inorganic powder, from 2 to 20% weight-% of the at least one binder, from 0.5 to 40 weight-% of the at least one plasticizing agent, optionally from 1 to 50 weight-% of the at least one pore-forming agent, optionally from 0.5 to 10 weight-% of the at least one surface active compound, and optionally from 20 to 90 weight-% of the at least one blowing agent precursor.

26. A method for the preparation of ethylene oxide which comprises utilizing the inorganic body according to claim 1 as a catalyst carrier.

27. The inorganic body of claim 1, wherein $R_A$ is in the range of from 0.35 to 0.65; $S_A$ is in the range of from 0.4 to 20 micrometer and $S_B$ is in the range of from 100 to 1000 micrometer; and the inorganic body comprising a specific surface area (BET) as determined according to DIN ISO 9277 in the range of from 0.8 to 1.2 m$^2$/g.

28. The inorganic body of claim 27, wherein the inorganic body comprises at least 95 weight-% alumina, of which at least 99 weight-% is comprised of alpha alumina.

29. The inorganic body of claim 27, comprising of from 200 to 750 weight-ppm of sodium, up to 600 weight-ppm, of silicon, and up to 100 weight-ppm of iron, based on the total weight of the inorganic body, calculated as element and as determined via elemental analysis.

30. A catalyst carrier or a catalyst which comprises the inorganic body of claim 27.

31. A porous inorganic body comprising pores A having a pore size $S_A$ in the range of from 0.1 to 20 micrometer and a total pore volume $V_A$, and pores B having a pore size $S_B$ in the range of from more than 100 to 1000 micrometer and a total pore volume $V_B$, wherein the total pore volume of the pores having a pore size in the range of from 0.005 to 1000 micrometer is $V_C$, and wherein a ratio $R_A = V_A/V_C$ is in the range of from 0.35 to 0.65 as determined via mercury intrusion porosimetry according to DIN 66133, and the differential intrusion exhibits at least one peak in the pore size range of from 0.1 to 20 micrometer and at least one peak in the pore size range of from 100 to 1000 micrometer, as determined via mercury intrusion porosimetry according to DIN 66133.

* * * * *